United States Patent
Pasternak et al.

(10) Patent No.: US 9,951,052 B2
(45) Date of Patent: Apr. 24, 2018

(54) INHIBITORS OF THE RENAL OUTER MEDULLARY POTASSIUM CHANNEL

(71) Applicant: Merck Sharp & Dohme Corp., Rahway, NJ (US)

(72) Inventors: Alexander Pasternak, Princeton, NJ (US); Haifeng Tang, Metuchen, NJ (US); Jessica Frie, Perkasie, PA (US); Ronald Dale Ferguson, Scotch Plains, NJ (US); Zhiqiang Guo, Morganville, NJ (US); Zhi-Cai Shi, Monmouth Junction, NJ (US); Brian Cato, Secaucus, NJ (US); Qinghong Fu, Plainsboro, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/032,174

(22) PCT Filed: Oct. 27, 2014

(86) PCT No.: PCT/US2014/062316
§ 371 (c)(1),
(2) Date: Apr. 26, 2016

(87) PCT Pub. No.: WO2015/065866
PCT Pub. Date: May 7, 2015

(65) Prior Publication Data
US 2016/0257670 A1    Sep. 8, 2016

Related U.S. Application Data

(60) Provisional application No. 61/898,073, filed on Oct. 31, 2013.

(51) Int. Cl.
| | | |
|---|---|---|
| *C07D 405/06* | (2006.01) |
| *A61K 31/4525* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 513/04* | (2006.01) |
| *A61K 31/427* | (2006.01) |
| *A61K 31/433* | (2006.01) |
| *A61K 31/4439* | (2006.01) |
| *A61K 31/454* | (2006.01) |
| *A61K 31/4545* | (2006.01) |
| *A61K 45/06* | (2006.01) |

(52) U.S. Cl.
CPC .......... *C07D 405/06* (2013.01); *A61K 31/427* (2013.01); *A61K 31/433* (2013.01); *A61K 31/4439* (2013.01); *A61K 31/454* (2013.01); *A61K 31/4525* (2013.01); *A61K 31/4545* (2013.01); *A61K 45/06* (2013.01); *C07D 405/14* (2013.01); *C07D 413/14* (2013.01); *C07D 417/14* (2013.01); *C07D 471/04* (2013.01); *C07D 513/04* (2013.01)

(58) Field of Classification Search
None
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |

(Continued)

FOREIGN PATENT DOCUMENTS

| | | | |
|---|---|---|---|
| WO | 2013039802 A1 | 3/2013 | |
| WO | WO 2013039802 A1 * | 3/2013 | ............ C07D 405/14 |

OTHER PUBLICATIONS

Felix. John. Assay and Drug Development Technologies, 2012, 10, 417-431.*
Bhave, Gautam. Molecular Pharmacology, 2011, 79, 42-50.*
Patani, George. Chem. Rev. (1996) 96, 3147-3176.*
Bhave,G., Development of a selective small-molecule inhibitor Kir1.1, the renal outer medullary potassium channel, Mol. Pharmacol., 2011, 42-50, 79.
Cheymol et al., Increase in the effects of epinephrine and acetylcholine . . . , Comptes Rendus des seances de la Societe de Biologie, 1951, 496-499 (English trans.), 145.
Dorwald, Side reactions in Organic Synthesis: A Guide to Successful Synthesis Design, 2005, Chapter 1.
Fallen, K., The Kir channel immunoglobuling domain is essential for Kir1.1 (ROMK) thermodynamic stability, trafficing and gating, Channels, 2009, 57-66, 3.

(Continued)

*Primary Examiner* — Deepak R Rao
*Assistant Examiner* — Laura M Daniel
(74) *Attorney, Agent, or Firm* — Sarah L. Hooson; Catherine D. Fitch

(57) ABSTRACT

The present invention provides compounds of Formula I

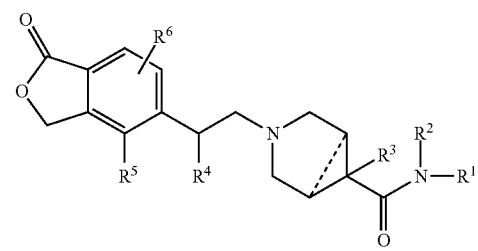

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

9 Claims, No Drawings

(56) References Cited

U.S. PATENT DOCUMENTS

| | | | |
|---|---|---|---|
| 5,145,885 | A | 9/1992 | Berner et al. |
| 5,215,989 | A | 6/1993 | Baldwin et al. |
| 5,614,526 | A | 3/1997 | Godel et al. |
| 5,736,546 | A | 4/1998 | Kawashima et al. |
| 6,258,813 | B1 | 7/2001 | Arlt et al. |
| 6,787,543 | B2 | 9/2004 | Take et al. |
| 8,673,920 | B2 | 3/2014 | Pasternak et al. |
| 8,952,166 | B2 | 2/2015 | Ding et al. |
| 2002/0013325 | A1 | 1/2002 | Fisher et al. |
| 2004/0110793 | A1 | 6/2004 | Lloyd et al. |
| 2004/0204404 | A1 | 10/2004 | Zelle et al. |
| 2005/0215526 | A1 | 9/2005 | Hulme et al. |
| 2005/0267121 | A1 | 12/2005 | Li et al. |
| 2006/0183739 | A1 | 8/2006 | Tsaklakidis et al. |
| 2006/0183742 | A1 | 8/2006 | Mederski et al. |
| 2006/0211692 | A1 | 9/2006 | Mederski et al. |
| 2007/0004750 | A1 | 1/2007 | Lorsbach et al. |
| 2007/0072865 | A1 | 3/2007 | Fukatsu et al. |
| 2007/0093472 | A1 | 4/2007 | Mederski et al. |
| 2007/0275990 | A1 | 11/2007 | Ohmoto et al. |
| 2008/0003214 | A1 | 1/2008 | Cezanne et al. |
| 2008/0090794 | A1 | 4/2008 | Dinsmore et al. |
| 2010/0286123 | A1 | 11/2010 | Pasternak et al. |
| 2013/0131042 | A1 | 5/2013 | Duffy et al. |
| 2015/0299198 | A1* | 10/2015 | Walsh ................ A61K 31/4184 514/210.18 |

OTHER PUBLICATIONS

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report of PCT/US2014/062316, dated Feb. 3, 2015; 8 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

PubChem Compound Summary for CID 7156526. Create Date: Jun. 6, 2013 [retrieve date Dec. 19, 2014]. Retrieved from <URL:http://pubchem.ncbi.nlm/nih.gov/compound/71516526#section=Top>.

Sica, D. A., Diuretic use in renal disease, Nature, 2012, 100-109, 8.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. § 371 of PCT Application No. PCT/US2014/062316 filed Oct. 27, 2014, which claims priority from U.S. Provisional Application Ser. No. 61/898,073, filed Oct. 31, 2013.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

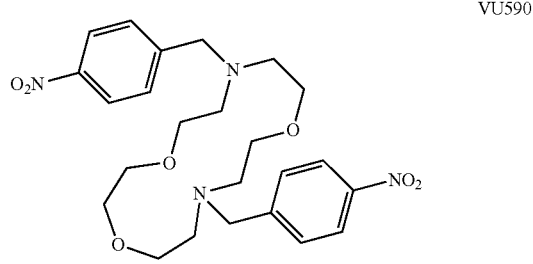

VU590

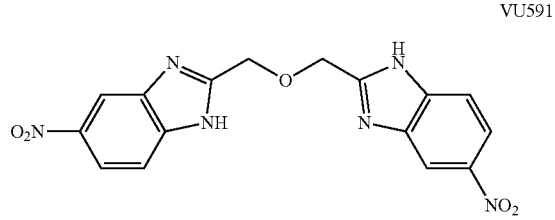

VU591

Patent application publication number WO2010/129379, published Nov. 11, 2010 having common representative Merck Sharp & Dohme Corp., (also published as US2010/0286123 on same date), describes ROMK inhibitors having the generic formula:

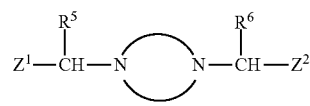

and, e.g., an embodiment

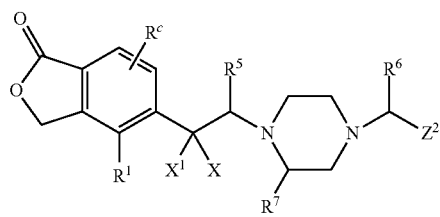

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

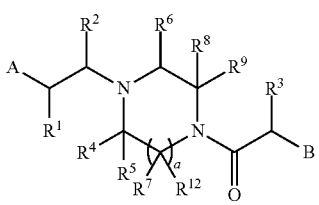

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

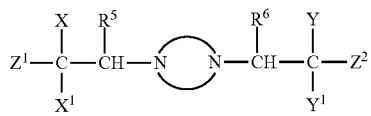

and, e.g., an embodiment

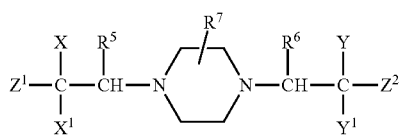

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

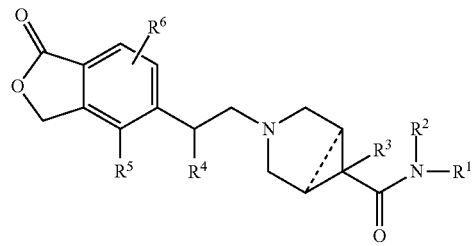

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

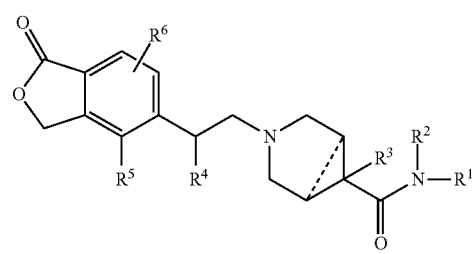

or a pharmaceutically acceptable salt thereof wherein:
$R^1$ is

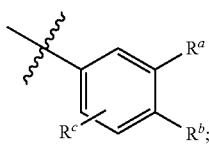

wherein one of $R^a$ and $R^b$ is —CN, tetrazolyl,

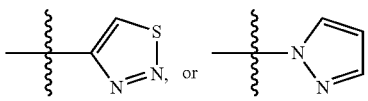

and the other is —H, halo, —$C_{1-6}$alkyl optionally substituted with one to three of —F, or —$OC_{1-6}$alkyl optionally substituted with one to three of —F; and $R^c$ is —H, halo, —C$_{1-6}$alkyl optionally substituted with one to three of —F, or —OC$_{1-6}$alkyl optionally substituted with one to three of —F;

(b)
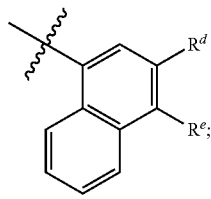

wherein one of R$^d$ and R$^e$ is —CN or tetrazolyl and the other is —H, halo, —C$_{1-3}$alkyl optionally substituted with one to three of —F or —OC$_{1-3}$alkyl optionally substituted with one to three of —F;

(c)
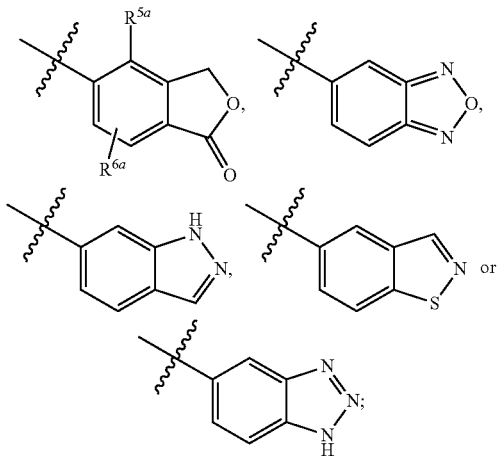

(d)
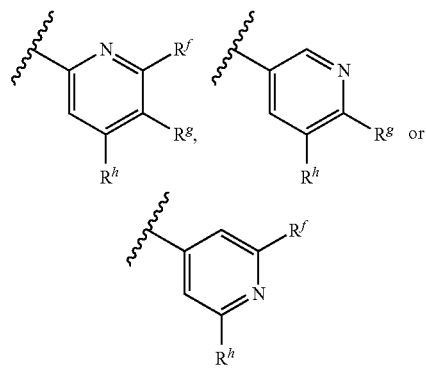

wherein
R$^f$ is —H, —C$_{1-6}$ alkyl, halo, —CN or tetrazolyl,
R$^g$ is —H, —C$_{1-6}$ alkyl, halo, —CN or tetrazolyl, and
R$^h$ is —H, —C$_{1-6}$ alkyl, halo, —CN or tetrazolyl,
provided that only one of R$^f$, R$^g$ or R$^h$ may be —CN or tetrazolyl;

(e) a 5 membered unsaturated heterocyclic ring containing carbon atoms and one to three heteroatoms independently selected at each occurrence from N, S or O, wherein the heterocyclic ring is (1) optionally substituted on an available ring carbon with —C$_{1-6}$alkyl, —OC$_{1-6}$alkyl, —C$_{3-6}$cycloalkyl, —OC$_{3-6}$cycloalkyl or —CN, and (2) optionally substituted on an available ring nitrogen with phenyl optionally substituted with one or more of —C$_{1-3}$alkyl and halo; or (f) a 5 membered unsaturated heterocyclic ring containing carbon atoms and one to three heteroatoms independently selected at each occurrence from N, S or O, which is fused to a pyridyl ring via two adjacent carbon atoms shared between the heterocyclic ring and the pyridyl ring, to form a 9 member hetero-bicyclic ring system;

R$^2$ is —H or —C$_{1-6}$alkyl;

or R$^1$ is a 6-membered ring, and R$^2$ is —(CH$_2$)$_n$— and is joined together with R$^1$ and the nitrogen to which they are both attached to form

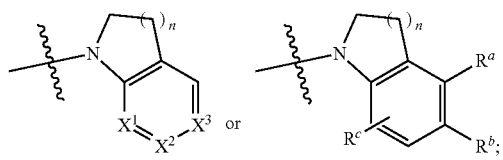

wherein R$^a$, R$^b$ and R$^c$ are as defined above;
one of X$^1$, X$^2$ or X$^3$ is N and the others are CH;
n is an integer selected from 1 or 2;
R$^3$ is —H, —OH, —F or —NH$_2$;
R$^4$ is —H, —OH, oxo, —F or —C$_{1-6}$alkyl;
R$^5$ is —H, halo or —C$_{1-3}$alkyl optionally substituted with one to three of —F;
R$^{5a}$ is —H, halo or —C$_{1-3}$alkyl optionally substituted with one to three of —F;
R$^6$ is —H, halo, —O—C$_{1-3}$alkyl, —C(O)OC$_{1-3}$alkyl or —C$_{1-3}$alkyl optionally substituted with one to three of —F;
R$^{6a}$ is —H, halo, —O—C$_{1-3}$alkyl, —C(O)OC$_{1-3}$alkyl or —C$_{1-3}$alkyl optionally substituted with one to three of —F; and
the dashed line "- - -" represents the presence or absence of a bond.

In an embodiment of this invention are compounds of Formula I and the pharmaceutically acceptable salts thereof wherein:
R$^1$ is (a)
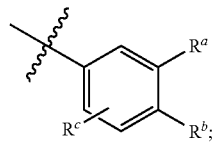

wherein one of R$^a$ and R$^b$ is —CN, tetrazolyl,

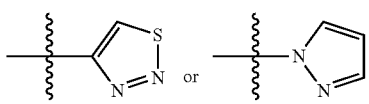 [SMILES: *c1csnn1 ; "or" ; *n1cccn1]

and the other is —H, —F, —Cl, —C$_{1-3}$alkyl or —OC$_{1-3}$ alkyl, and R$^c$ is —H, —F, —Cl, —C$_{1-3}$alkyl substituted with one to three of —F, or —OC$_{1-3}$alkyl optionally substituted with one to three of —F;

(b) 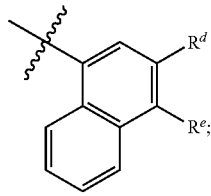

wherein one of R$^d$ and R$^e$ is —CN and the other is —H, halo, —C$_{1-3}$alkyl or —OC$_{1-3}$alkyl, and particularly it is —H;

(c) 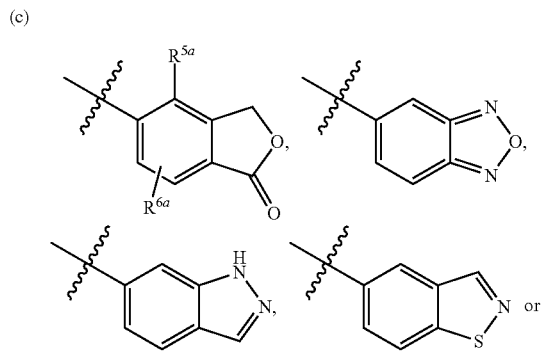

(d) 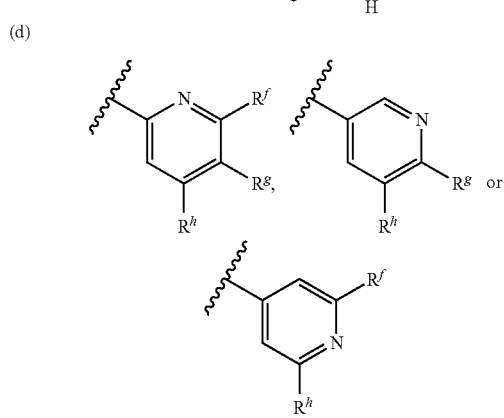

wherein
R$^f$ is —H, —C$_{1-3}$ alkyl, —F or —Cl;
R$^g$ is —H, —CN or tetrazolyl,
R$^h$ is —H, —C$_{1-3}$ alkyl, —F or —Cl;
e) a 5 membered heterocyclic ring selected from:

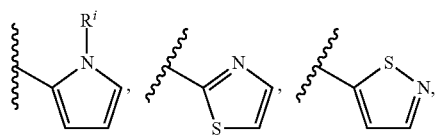

-continued

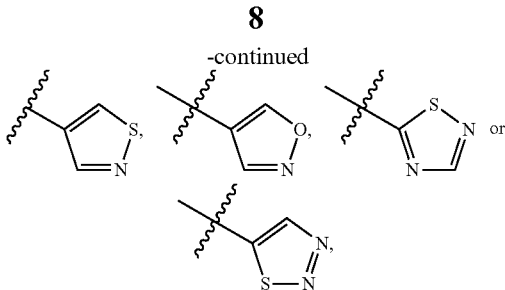

wherein each heterocyclic ring is optionally substituted on an available ring carbon with —C$_{1-3}$alkyl, —OC$_{1-3}$alkyl, —C$_{3-4}$cycloalkyl, —OC$_{3-4}$cycloalkyl or —CN; and R$^i$ is selected from —H or phenyl optionally substituted with C$_{1-3}$alkyl or halo; or f) 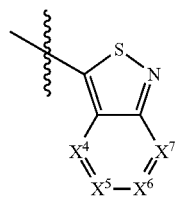

wherein one of X$^4$, X$^5$, X$^6$ or X$^7$ is N and the others are CH, and particularly it is

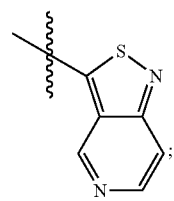 [SMILES: *c1snc2ccncc12]

R$^2$ is —H or —C$_{1-3}$alkyl;
or R$^1$ is pyridyl, and R$^2$ is —(CH$_2$)$_n$— and is joined together with R$^1$ and the nitrogen to which they are both attached to form

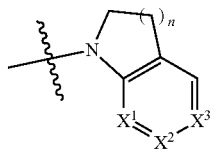

wherein one of X$^1$, X$^2$ or X$^3$ is N and the others are CH;
R$^3$ is —H, —OH, —F or —NH$_2$;
R$^4$ is —H or —OH;
R$^5$ is —H, halo, —CH$_3$ or —CF$_3$, and particularly it is —H or —CH$_3$;
R$^{5a}$ is —H, halo, —CH$_3$ or —CF$_3$, and particularly it is —H or —CH$_3$;
R$^6$ is —H;
R$^{6a}$ is —H; and the dashed line "- - -" represents the presence or absence of a bond;
wherein all other variables are as defined in Formula I.

In another embodiment of this invention are compounds of Formula I and the pharmaceutically acceptable salts thereof wherein:
$R^1$ is

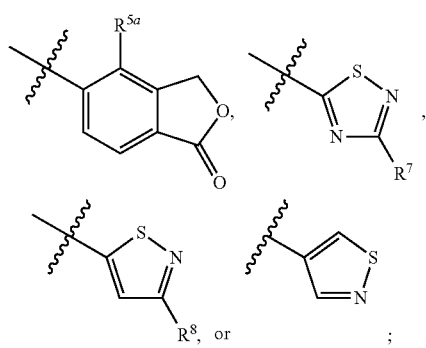

$R^2$ is —H or —$C_{1-3}$alkyl;
$R^3$ is —H, —F or —$NH_2$;
$R^4$ is —H or —OH;
$R^5$ is —H, halo, —$CH_3$ or —$CF_3$, and particularly it is —H or —$CH_3$;
$R^{5a}$ is —H, halo, —$CH_3$ or —$CF_3$, and particularly it is —H or —$CH_3$;
$R^6$ is —H;
$R^7$ is —H, —$C_{1-3}$alkyl or —$OC_{1-3}$alkyl;
$R^8$ is —H, —$C_{1-3}$alkyl or —$OC_{1-3}$alkyl; and
the dashed line "- - -" represents the presence or absence of a bond;
wherein all other variables are as defined in Formula I.

In another embodiment of this invention are compounds of Formula I and the pharmaceutically acceptable salts thereof wherein $R^1$ is

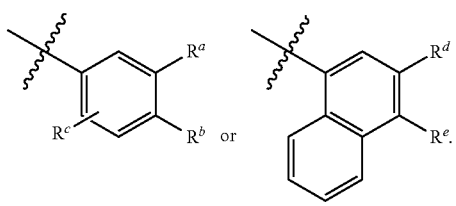

In another embodiment of this invention are compounds of Formula I and the pharmaceutically acceptable salts thereof wherein $R^1$ is

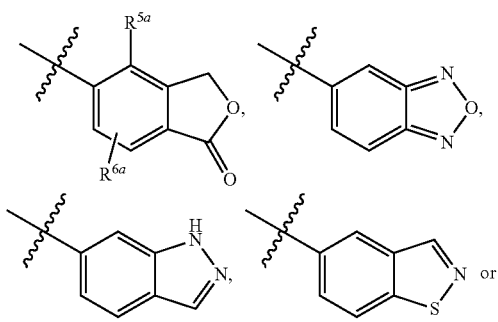

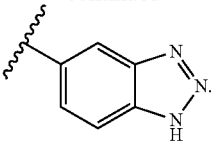

In another embodiment of this invention are compounds of Formula I and the pharmaceutically acceptable salts thereof wherein $R^1$ is

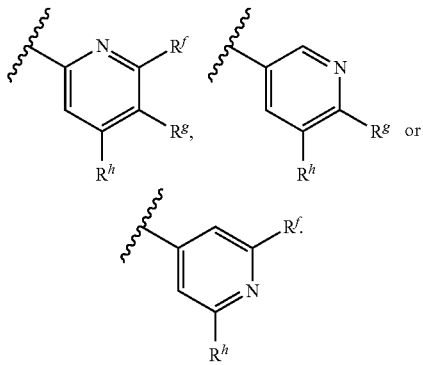

In another embodiment of this invention are compounds of Formula I and the pharmaceutically acceptable salts thereof wherein $R^1$ is a 5 membered unsaturated heterocyclic ring containing carbon atoms and one to three heteroatoms independently selected at each occurrence from N, S or O, wherein the heterocyclic ring is:
(A) optionally substituted on an available ring carbon with —$C_{1-6}$alkyl, —$OC_{1-6}$alkyl, —$C_{3-6}$cycloalkyl, —$OC_{3-6}$cycloalkyl or —CN, and optionally substituted on an available ring nitrogen with phenyl optionally substituted with one or more of $C_{1-3}$alkyl and halo; or
(B) fused to a pyridyl ring via two adjacent carbons shared between the heterocyclic ring and the pyridyl ring, to form a 9 member hetero-bicyclic ring system.

In another embodiment of this invention are compounds of Formula I and the pharmaceutically acceptable salts thereof wherein $R^1$ is pyridyl, and $R^2$ is —$(CH_2)_2$— and is joined together with $R^1$ and the nitrogen to which they are both attached to form

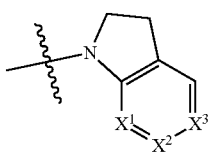

and particularly it is:

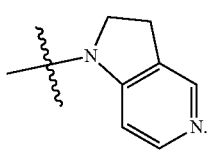

In a further embodiment of Formula I, R$^1$ is

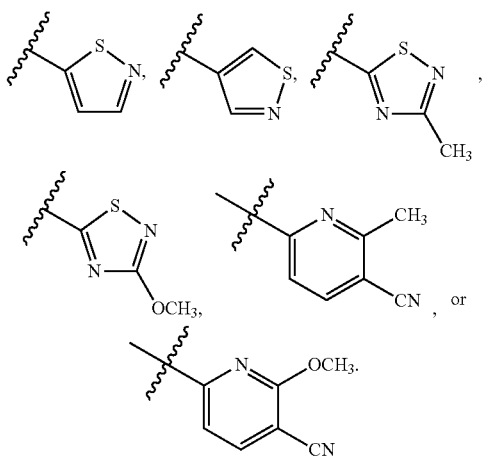

In a further embodiment of Formula I and of each additional embodiment described herein, R$^2$ is —H or —CH$_3$.

In a further embodiment of Formula I and of each additional embodiment described herein, R$^3$ is —H or —F.

In a further embodiment of Formula I and of each additional embodiment described herein, R$^4$ is —H or —OH.

In a further embodiment of Formula I and of each additional embodiment described herein, R$^5$ is —CH$_3$.

In a further embodiment of Formula I and of each additional embodiment described herein, R$^{5a}$ is —H or —CH$_3$ In a further embodiment of Formula I and of each additional embodiment described herein, R$^6$ is —H.

In a further embodiment of Formula I and of each additional embodiment described herein, R$^{6a}$ is —H.

All structural Formulas, embodiments and classes thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "C$_{1-6}$ alkyl" (or "C$_1$-C$_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I. Fluoro or chloro are preferred.

Unless expressly depicted or described otherwise, variables depicted in a structural formula with a "floating" bond, such as R$^c$, are permitted on any available carbon atom in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and compounds that do not contain the noted substituent (or substituents) on the moiety.

Reference to the compounds of Formula I herein encompasses those compounds and all embodiments and classes thereof. Reference to the compounds of this invention as those of a specific formula or embodiment or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 μM or less, preferably 1 μM or less, and more preferably 0.25 μM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S), 5(S),7(S)-N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mono-nitrate; lipid lowering agents, e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. In the following Schemes, the "R" substituents correspond to the substituents defined in Formula I at the same positions on the structures; "P" is used to denote a protective group, for example ethyl or methyl ester to protect the carboxylic acid; and the dashed line represents the optional presence of a bond.

Several methods for preparing the compounds of this invention are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

One method for the preparation of the compounds of the Formula I is detailed in Scheme 1. According to the Scheme, aminoesters 1 are subjected to reductive alkylation with aldehydes or ketones 2 using any of a variety of reagents such as sodium cyanoborohydride, sodium triacetoxyborohydride, or Ti(O-iPr)$_4$, followed by sodium borohydride. The resulting amines 3a can be hydrolyzed to the corresponding carboxylic acids 4a in a variety of ways depending upon what the protective group (P) is (Greene, T.; Wuts, P. G. M. *protective Groups in Organic Synthesis*, John Wiley and Sons, Inc., New York, N.Y. 1991). For example tert-butyl esters can be treated with an acid such as TFA, benzyl esters can by subjected to hydrogenolysis using hydrogen gas in the presence of a catalyst such as palladium on carbon, and methyl or ethyl esters can be hydrolyzed by treatment with a base such as LiOH, NaOH, or KOH. Then aromatic or heterocyclic amines 5 (H$_2$N—R$^1$) are coupled with carboxylic acids 4a, to afford amides of the Formula Ia. Such amide coupling reactions can be conducted using numerous experimental conditions known to the chemist. For example, conversion of the carboxylic acid to an acid chloride followed by treatment with amines 5 often in the presence of a base such as triethylamine or N,N-diisopropylethylamine can afford amides Ia. Or coupling of the carboxylic acid 4a and amine 5 can be achieved using one of many amide coupling reagents such as EDCI, HBTU or HATU to afford compounds of the Formula Ia.

SCHEME 1

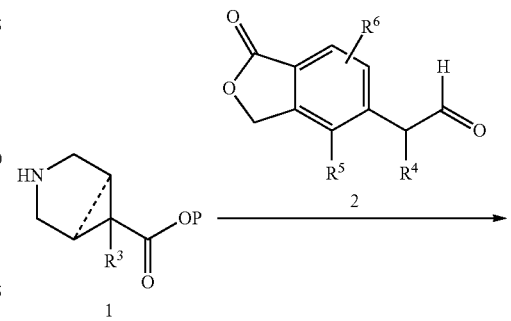

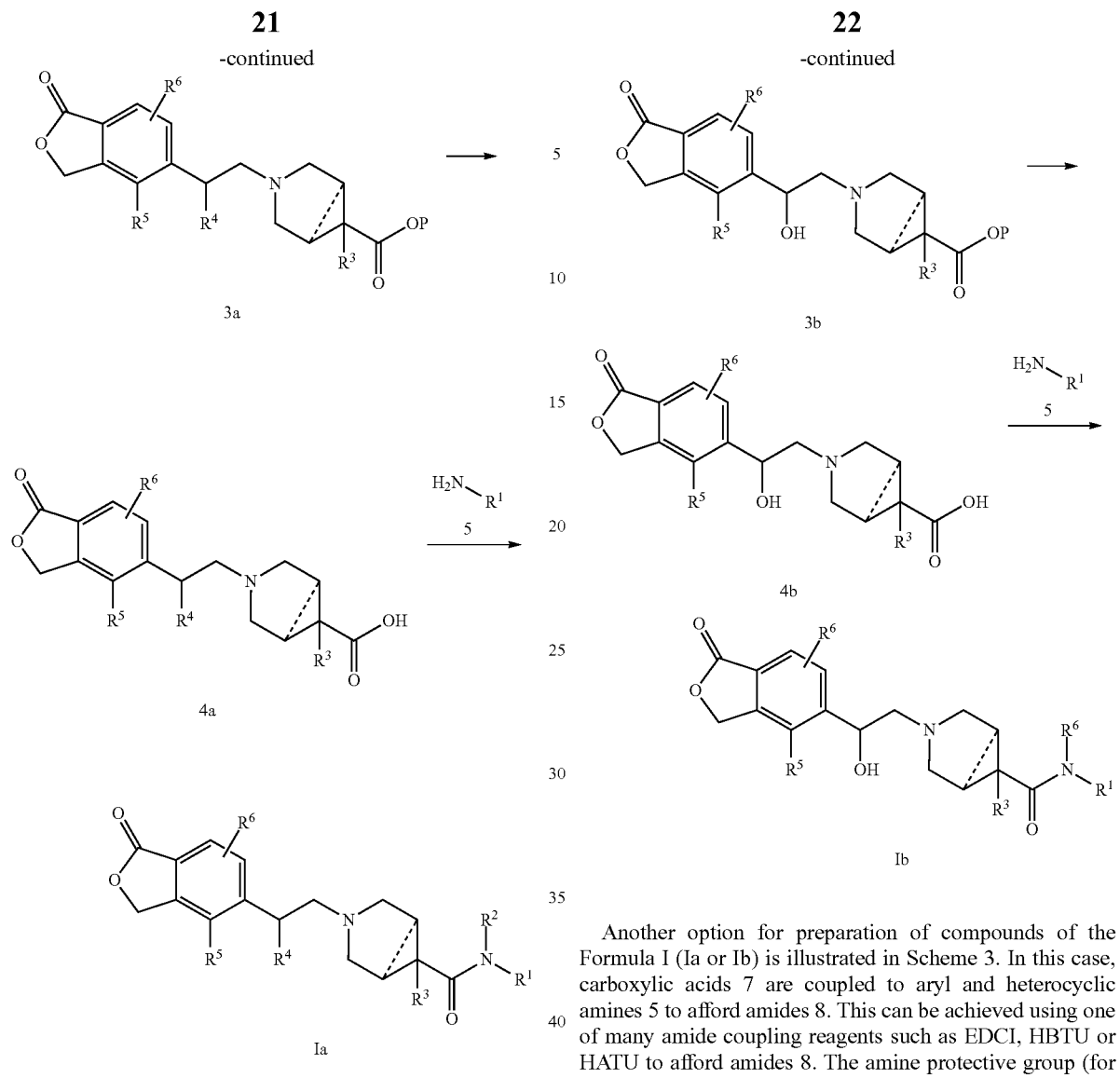

Alternatively, compounds of the Formula I (Ib) can be prepared according to Scheme 2. As illustrated, amines 1 are combined with epoxides 6, often with heating, to afford hydroxyamines 3b. The hydroxyamines 3b are hydrolyzed (4b) and coupled to amines 5 in an analogous fashion as described in Scheme 1 to afford the compounds of the Formula Ib.

SCHEME 2

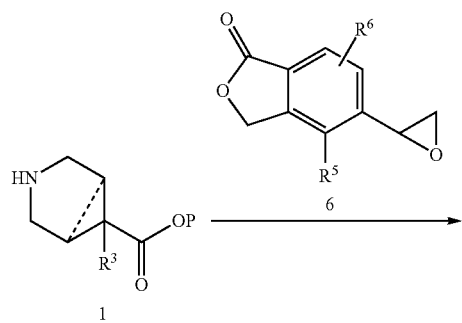

Another option for preparation of compounds of the Formula I (Ia or Ib) is illustrated in Scheme 3. In this case, carboxylic acids 7 are coupled to aryl and heterocyclic amines 5 to afford amides 8. This can be achieved using one of many amide coupling reagents such as EDCI, HBTU or HATU to afford amides 8. The amine protective group (for example in this illustration, Boc, but other protective groups known to the chemist can be substituted) is then removed to afford aminoamides 9. In the case of a Boc protective group this is accomplished under acidic conditions, for example, with HCl or trifluoroacetic acid. Aminoamides 9 are subjected to reductive alkylation with aldehydes or ketones 2 using any of a variety of reagents such as sodium cyanoborohydride, sodium triacetoxyborohydride, or Ti(O-iPr)$_4$, followed by sodium borohydride to afford compounds of the Formula Ia. Alternatively, aminoamides 9 are combined with epoxides 6, generally with heating, to afford compounds of the Formula Ib.

SCHEME 3

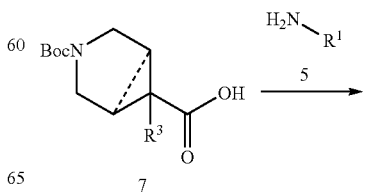

-continued

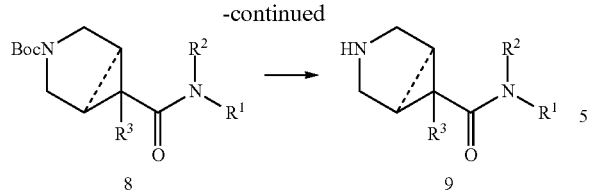

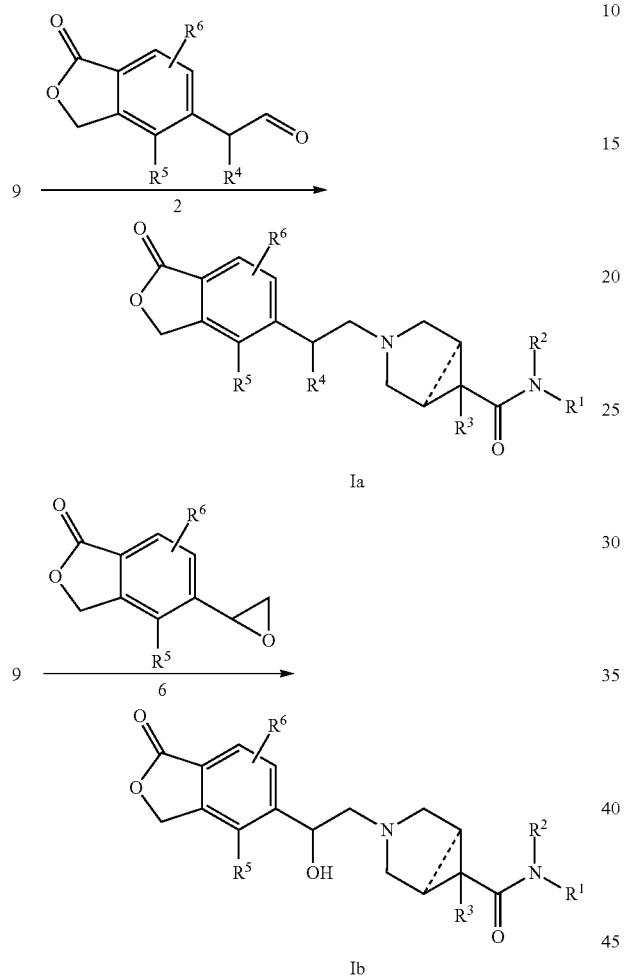

In instances where $R^2$ is alkyl, compounds of the Formula Ia or Ib can be prepared as outlined in Scheme 4. Intermediate 8a (prepared as described in Scheme 3) is treated with a base, such as sodium hydride, in a solvent such as dimethyl formamide, to afford tertiary amides 8b. Tertiary amides 8b can then be carried forward to compounds of the Formula I, in the same fashion as described in Scheme 3.

SCHEME 4

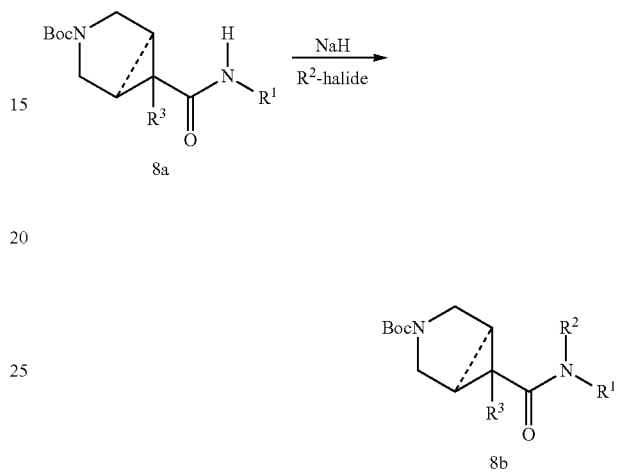

Intermediates 2 and 6 can be prepared according to Scheme 5. According to the Scheme, bromobenzolactones 10, which are commercially available or prepared as described herein and elsewhere, are converted to the allyl (11) or vinyl (12) intermediates using palladium catalyzed coupling with allyltin reagents or potassium vinyl trifluoroborates, respectively. While bromide 10 is illustrated, as known to the chemist, bromide can be substituted by chloro, iodo, or triflate (among others). Allyl intermediates 11 can be converted to aldehydes and ketones 2 in various ways, including by ozonolysis, followed by treatment with dimethyl sulfide (DMS) or triphenyl phosphine. Vinyl intermediates 12 can be transformed to epoxides 6 in several ways, including by treatment with meta-chloroperoxybenzoic acid (mCPBA).

SCHEME 5

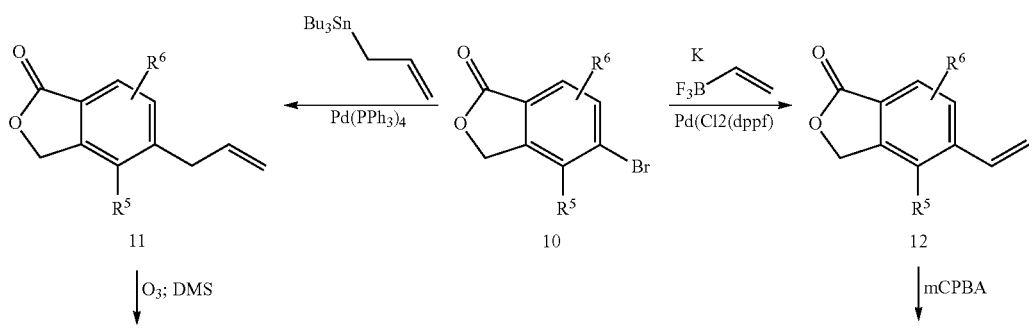

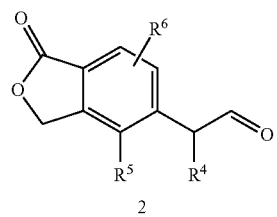

2

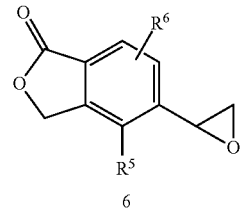

6

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times (or order of elution) are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used. Concentration of solutions was generally carried out on a rotary evaporator under reduced pressure Crystallization or recrystallization techniques are intended to describe a purification procedure that was used, but do not imply that the resulting product obtained from the procedure is crystalline.

Abbreviations and acronyms that may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); benzyl (Bn); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); deuterium ($^2$H, or D); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); diethyl amine (DEA); dimethoxyethane (DME); Diisobutylaluminium hydride (DIBAL-H); N,N-diisopropylethylamine (DIEA, DIPEA, Hunig's base); dioxane is 1,4-dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-Bis(diphenylphosphino)propane (DPPP);

(Oxydi-2,1-phenylene)bis(diphenylphosphine) (DPEPhos); ethyl acetate (EtOAc or EA); diethyl ether (ether or Et$_2$O); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); O-(Benzotriazol-1-yl)-N,N,N',N'-tetramethyluronium hexafluorophosphate, also known as N-[(1H-benzotriazol-1-yloxy)(dimethylamino)methylidene]-N-methylmethanaminium hexafluorophosphate (HBTU); hexane (Hex); hexamethylphosphoramide (HMPA); 1-Hydroxybenzotriazole hydrate (HOBt); isopropanol (IPA); isopropyl acetate (IPAc); lithium aluminum hydride (LAH); lithium diisopropylamide (LDA); 3-chloroperoxybenzoic acid (mCPBA); methanol (MeOH); CH$_3$SO$_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-Bis(diphenylphosphino)ferrocene]dichloropalladium(II) which may be complexed with CH$_2$Cl$_2$; tetra-n-butylammonium fluoride (TBAF); tert-butyldimethylsilyl chloride (TBS-Cl); triethylamine (TEA, Et$_3$N); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); p-toluenesulfonic acid (TsOH or PTSA); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); ultra-performance liquid chromatography (UPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time (R$_t$); gram(s) (g); milligram(s) (mg); milliliter(s) (mL); microliter(s) (µL); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which generally refers to the observed faster eluting isomer unless stated otherwise, and isomer B (or enantiomer B or the like), which refers to the observed slower eluting isomer unless stated otherwise, and each such isomer may be noted in the example as either the fast or slow eluting isomer. When a single "A" or "B" isomer intermediate is used to prepare a downstream compound, the downstream compound will take the "A" or "B" designation that corresponds to the previously used intermediate. Any Intermediates described below may be referred to herein by their number preceded by "I-." For illustration, in the example titled "Intermediate 4," the racemic parent title compound would be referred to as Intermediate 4 (or I-4), and the separated stereoisomers are noted as Intermediates 4A and 4B (or I-4A and I-4B). Except for a defined chiral center that may be present in a parent isomer mixture, absolute stereochemistry (R or S) of each of the separated isomers was not determined, unless specifically described otherwise. An asterisk (*) may be used in a chemical structure drawing that indicates the location of a chiral center.

INTERMEDIATE 1

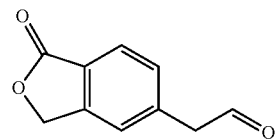 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, Firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo (1,3-dioxolan-2-ylmethyl)zinc solution (1.03 L, 516 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO$_4$, filtered, and concentrated. The crude product was purified by flash chromatography (1.5 kg silica cartridge), eluting with 0-20% ethyl acetate in dichlromethane to afford 5-(1,3-dioxolan-2-ylmethyl)-2-benzofuran-1 (3H)-one.

LC-MS (IE, m/z): 221 [M+1]$^+$.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde.

LC-MS (IE, m/z): 177 (M+1)$^+$.

INTERMEDIATE 2

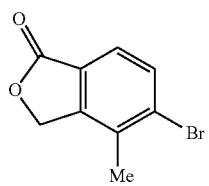 [SMILES: Cc1c(Br)ccc2c1COC2=O]

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The solution was filtered through a CELITE® pad, washed with EtOAc, adsorbed onto silica and purified by silica gel chromatography to afford 5-bromo-4-methyl-2-benzofuran-1(3H)-one. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

INTERMEDIATE 3

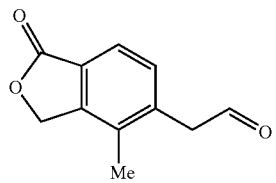 [SMILES: Cc1c(CC=O)ccc2c1COC2=O]

(4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 ml, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1 (3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol).

The reaction was allowed to warm up to RT. The crude product was purified by flash chromatography to afford (4-methyl-1-oxo-1,3-dihydro-2-benzofuran-5-yl)acetaldehyde. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 4

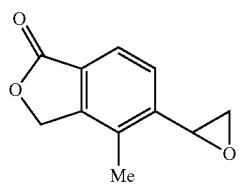 [SMILES: Cc1c(C2CO2)ccc2c1COC2=O]

4-methyl-5-oxiran-2-yl-2-benzofuran-1 (3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$ adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03(dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1 (3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=191.

INTERMEDIATES 4A AND 4B (METHOD 1)

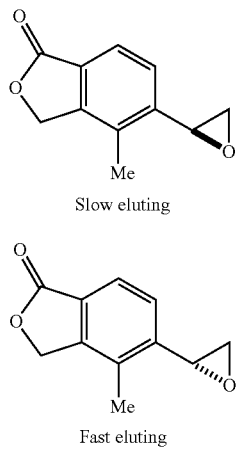

4A: 4-methyl-5-[(2S)-oxiran-2-yl]-2-benzofuran-1 (3H)-one

4B: 4-methyl-5-[(2R)-oxiran-2-yl]-2-benzofuran-1 (3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/ml in 1:1 DCM:MeOH. The separation was accomplished using 10% EtOH/CO$_2$, flow rate 200 ml/min, 100 bar, 25° C. 500 ul Injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1(3H)-one, 4A) eluted second.

Alternatively, the resolution could also be achieved using a mobile phase of 8% MeOH/98% CO$_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 4B and by Mosher ester and Trost ester HNMR analysis of esters made starting from 4B.

INTERMEDIATE 4B (METHOD 2)

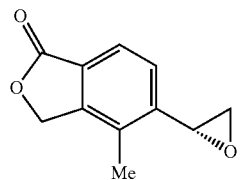 [SMILES: Cc1c([C@@H]2CO2)ccc2c1COC2=O]

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the solids were washed with 4:1 heptane: MTBE (500 mL), followed by heptane (500 mL). The solid was dried under vacuum, providing 4-bromo-3-hydroxymethyl-2-methyl phenol.

Step C:
5-Hydroxy-4-methyl-3H-isobenzofuran-1-one

To a 2 L 3 neck flask equipped with overhead stirrer, $N_2$ inlet, and condenser were charged 4-bromo-3-hydroxymethyl-2-methyl phenol (100 g, 461 mmol), CuCN (83.0 g, 921 mmol), and DMF (500 mL). The solution was sparged with $N_2$ for 15 min then heated to 145° C. to obtain a homogeneous solution. The solution was aged at 145° C. for 2 h, then the reaction mixture was cooled to 95° C. 41.5 mL water was added (sparged with $N_2$), and the reaction aged for 20 h. The reaction was cooled to RT then the solids filtered through SOLKA FLOC® and the cake washed with 50 mL DMF. To a 3 L flask containing 1 L EtOAc was added the DMF filtrate. A precipitate coating formed in bottom of flask. The DMF/EtOAc suspension was filtered through SOLKA FLOC® and the cake was washed with 250 mL EtOAc. The resulting filtrate was washed with 5% brine solution (3×500 mL). The aqueous layers were extracted with 500 mL EtOAc and the combined organics were dried over $MgSO_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

Step D: Trifluoromethanesulfonic acid 4-methyl-1-oxo-1,3-dihydro-isobenzofuran-5-yl ester 5-Hydroxy-4-methyl-3H-isobenzofuran-1-one (46.8 g, 285 mmol) was suspended in dichloromethane (935 mL) in 2-L round bottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over SOLKA FLOC®, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product precipitating during concentration. The suspension was filtered, the solid washed with heptane and dried under vacuum and nitrogen, providing the title compound.

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) then $Et_3N$ (35.6 mL, 255 mmol). The solution was sparged with $N_2$ for 20 min. To the solution was added $Pd(OAc)_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% $NH_4Cl$ (2×315 mL), 10% brine (2×315 mL), dried over $MgSO_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one.

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck RB flask equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/ 5:1 Hexanes:IPAc solution (150 mL). The solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

INTERMEDIATE 5

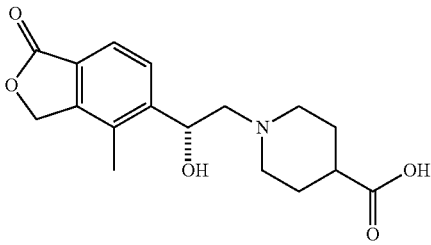 [SMILES: Cc1c([C@@H](O)CN2CCC(C(=O)O)CC2)ccc2c1COC2=O]

(R)-1-(2-hydroxy-2-(4-methyl-1-oxo-1,3-dihydroisobenzofuran-5-yl)ethyl)piperidine-4-carboxylic acid Step A: (R)-tert-butyl 1-(2-hydroxy-2-(4-methyl-1-oxo-1,3-dihydroisobenzofuran-5-yl)ethyl)piperidine-4-carboxylate A mixture of tert-butyl piperidine-4-carboxylate (0.40 g, 2.2 mmol) and (R)-4-methyl-5-(oxiran-2-yl)isobenzofuran-1(3H)-one (0.82 g, 4.3 mmol) in EtOH (5 mL) was heated to 140° C. for 1 hour. LC showed complete reaction. The reaction was concentrated to dryness and the residue was purified by silica gel chromatography to afford the title compound. LCMS: 376 (M+1)$^+$.

Step B: (R)-1-(2-hydroxy-2-(4-methyl-1-oxo-1,3-dihydroisobenzofuran-5-yl)ethyl)piperidine-4-carboxylic acid To a flask charged with (R)-tert-butyl 1-(2-hydroxy-2-(4-methyl-1-oxo-1,3-dihydroisobenzofuran-5-yl)ethyl)piperidine-4-carboxylate (68 mg) was added TFA (1 mL). The mixture was allowed to stand at RT for 30 minutes. The volatiles were removed under vacuum, and the residue was azeotroped with DCE. The resulting solids were used without further purification. LCMS: 320 (M+1)$^+$.

INTERMEDIATE 6

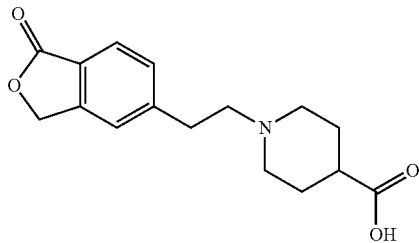 [SMILES: O=C1OCc2cc(CCN3CCC(C(=O)O)CC3)ccc21]

1-(2-(1-oxo-1,3-dihydroisobenzofuran-5-yl)ethyl)piperidine-4-carboxylic acid

Step A: 1-benzyl 4-tert-butyl piperidine-1,4-dicarboxylate 1-((Benzyloxy)carbonyl)piperidine-4-carboxylic acid (10 g, 38.0 mmol) was dissolved in toluene (100 ml) and warmed to 800 then added N,N dimethylformamide-di-t-butyl acetal (36.4 ml, 152 mmol) and heated for 1 hr. After all starting materials were consumed, the reaction was poured into 1N HCl and extracted with EtOAc (2×). The combined organics were washed with brine then dried over Na$_2$SO$_4$ and concentrated to yield 1-benzyl 4-tert-butyl piperidine-1,4-dicarboxylate.
$^1$H-NMR (500 MHz, CDCl$_3$) δ ppm 7.32-7.39(m, 5H), 5.153 (s, 2H), 4.096 (b, 2H), 2.954 (b, 2H), 2.36-2.421 (m, 1H), 1.878 (b, 2H), 1.486-1.675 (m, 2H), 1.468 (s, 9H).

Step B: tert-butyl piperidine-4-carboxylate

1-Benzyl 4-tert-butyl piperidine-1,4-dicarboxylate (11.3 g, 35.4 mmol) was dissolved in ethyl acetate (120 ml), Pd/C was added (2.0 g, 18.79 mmol), then the mixture was hydrogenated at 20° C., 40 psi for 18 hrs. The reaction mixture was filtered and concentrated to yield tert-butyl piperidine-4-carboxylate. $^1$H-NMR (500 MHz, CDCl$_3$) δ ppm 3.0825 (d, J=12.5 Hz, 2H), 2.625 (t, J=12 Hz, 2H), 2.281-2.341 (m, 1H), 1.846 (d, J=13.5 Hz, 2H), 1.681(b, 1H), 1.558-1.608(m, 1H), 1.447 (s, 9H).

Step C: tert-butyl 1-(2-(1-oxo-1,3-dihydroisobenzofuran-5-yl)ethyl)piperidine-4-carboxylate tert-Butyl piperidine-4-carboxylate (2.84 g, 15.33 mmol) and 2-(1-oxo-1,3-dihydroisobenzofuran-5-yl)acetaldehyde (4.05 g, 22.99 mmol) were dissolved in DCE (120 ml) then sodium triacetoxyborohydride (9.75 g, 46.0 mmol) was added and and the mixture was stirred for 16 hrs. The reaction mixture was poured into aqueous NaHCO$_3$ solution and extracted with DCM. The organic layer was separated and dried over Na$_2$SO$_4$, filtered and concentrated. The crude residue was chromatographed through a 330 g ISCO Redi-sep column and eluted with 5% (NH$_4$OH: MeOH 1:9) in 95% DCM to yield tert-butyl 1-(2-(1-oxo-1,3-dihydroisobenzofuran-5-yl)ethyl)piperidine-4-carboxylate.
LC-MS (IE, m/z): 346 [M+1]$^+$; $^1$H-NMR (500 MHz, CDCl$_3$) δ ppm 7.859 (d, J=7.9 Hz, 1H), 7.394 (d, J=8.0 Hz, 1H), 7.352 (s, 1H), 5.311 (s, 2H), 2.965 (b, 4H), 2.641 (b, 2H), 2.234 (b, 1H), 2.139 (b, 2H), 1.925(d, J=9.5 Hz, 2H), 1.788(t, J=11.5 Hz, 2H), 1.447 (s, 9H).

Step D: 1-(2-(1-oxo-1,3-dihydroisobenzofuran-5-yl) ethyl)piperidine-4-carboxylic acid tert-Butyl 1-(2-(1-oxo-1,3-dihydroisobenzofuran-5-yl) ethyl)piperidine-4-carboxylate (4.21 g, 12.19 mmol) was dissolved in dioxane (30 ml), then HCl (15 ml, 60.0 mmol) was added and the mixture was stirred 16 hrs. The reaction mixture was concentrated then triturated with methylene chloride, then the solids were filtered off to obtain 1-(2-(1-oxo-1,3-dihydroisobenzofuran-5-yl)ethyl)piperidine-4-carboxylic acid. LC-MS (IE, m/z): 298 [M+1]$^+$

INTERMEDIATE 7

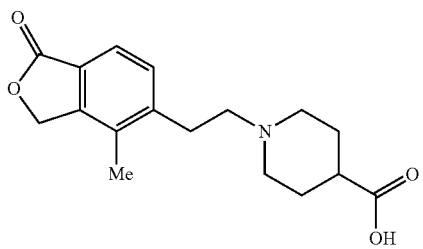 [SMILES: Cc1c(CCN2CCC(C(=O)O)CC2)ccc2c1COC2=O]

1-(2-(4-methyl-1-oxo-1,3-dihydroisobenzofuran-5-yl)ethyl)piperidine-4-carboxylic acid Step A: tert-butyl 1-(2-(4-methyl-1-oxo-1,3-dihydroisobenzofuran-5-yl)ethyl)piperidine-4-carboxylate A solution of 2-(4-methyl-1-oxo-1,3-dihydroisobenzofuran-5-yl)acetaldehyde (3.20 g, 16.8 mmol), tert-butyl piperidine-4-carboxylate (3.10 g, 16.8 mmol) and AcOH (2 drops) in MeOH (15 mL) was stirred at 70° C. for 1 hour. Then NaCNBH$_3$ (3.10 g, 50.4 mmol) was added. The reaction mixture was stirred at 70° C. overnight. After cooling to r.t., the mixture was concentrated in vacuo. The mixture was filtered and purified by column chromatography to afford the title product.

Step B: 1-(2-(4-methyl-1-oxo-1,3-dihydroisobenzofuran-5-yl)ethyl)piperidine-4-carboxylic acid A solution of tert-butyl 1-(2-(4-methyl-1-oxo-1,3-dihydroisobenzofuran-5-yl)ethyl)piperidine-4-carboxylate (3.0 g, 8.34 mmol) in HCl/dioxane (15 mL) was stirred at r.t. for 1 hour. The mixture was then concentrated under reduced pressure to afford the title compound.

INTERMEDIATE 8

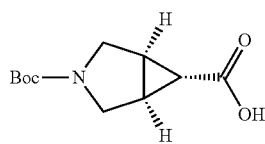 [SMILES: CC(C)(C)OC(=O)N1C[C@@H]2[C@H](C1)[C@H]2C(=O)O]

3-(tert-butoxycarbonyl)-3-aza-bicyclo[3.1.0]hexane-6-carboxylic acid

Step A: ethyl 5-benzyl-4,6-dioxo-1,3a,4,5,6,6a-hexahydropyrrolo[3,4-c]pyrazole-3-carboxylate Into a 5-L 4-necked round-bottom flask was placed a solution of 1-benzyl-1H-pyrrole-2,5-dione (175 g, 935.83 mmol, 1.00 equiv.) in 2 L Et$_2$O at room temperature. This was followed by the addition of a solution of ethyl diazoacetate (127 g, 1.10 mol, 1.00 equiv.) in 500 mL Et$_2$O dropwise with stirring at room temperature over 20 minutes. The resulting solution was stirred for 4 days at room temperature, then concentrated under vacuum. This afforded ethyl 5-benzyl-4,6-dioxo-1,3a,4,5,6,6a-hexahydropyrrolo[3,4-c]pyrazole-3-carboxylate. LC-MS (ES, m/z): 302 [M+H]$^+$.

Step B: ethyl 3-benzyl-2,4-dioxo-3-aza-bicyclo [3.1.0]hexane-6-carboxylate

Ethyl 5-benzyl-4,6-dioxo-1,3a,4,5,6,6a-hexahydropyrrolo[3,4-c]pyrazole-3-carboxylate (100 g, 332.23 mmol, 1.00 equiv.) was added to a flask heated at 190° C. over a period of 1 hour. The reaction mixture was cooled to room temperature and diluted with 250 mL of Et$_2$O. The resulting mixture was stirred overnight at room temperature and then cooled to −50° C. The isolated solid was collected and washed with 3×50 mL of Et$_2$O. This afforded the title compound.

Step C: ethyl 3-benzyl-3-aza-bicyclo[3.1.0]hexane-6-carboxylate

Into a 20-L 4-neck round-bottom flask purged and maintained with an inert atmosphere of nitrogen was placed a solution of ethyl 3-benzyl-2,4-dioxo-3-aza-bicyclo[3.1.0] hexane-6-carboxylate (650 g, 2.38 mol, 1.00 equiv.) in 3500 mL tetrahydrofuran, then a suspension of NaBH$_4$ (271.4 g, 7.14 mol, 3.00 equiv.) in 300 mL tetrahydrofuran was added. This was followed by the addition of BF$_3$.Et$_2$O (1342.3 g, 9.52 mol, 4.00 equiv.) dropwise with stirring at −15° C. over 60 minutes. The resulting solution was stirred for 1.5 hours at 20-35° C., then quenched by the addition of water and saturated NH$_4$Cl solution. The resulting mixture was concentrated under vacuum. The residual solution was extracted with 3×2000 mL of ethyl acetate. The organic layers were combined, washed with 2×1000 mL of brine, dried over anhydrous sodium sulfate and concentrated under vacuum. This afforded the title compound. LC-MS (ES, m/z): 246 [M+H]$^+$.

Step D: ethyl 3-aza-bicyclo[3.1.0]hexane-6-carboxylate

A mixture of ethyl 3-benzyl-3-aza-bicyclo[3.1.0]hexane-6-carboxylate (344 g, 982.86 mmol, 1.00 equiv., 70%), NH$_4$COOH (530.7 g, 8.42 mol, 6.00 equiv.) and palladium carbon (206.4 g, 10%) in methanol (2500 mL) was stirred for 90 minutes at 50° C. in an oil bath. The reaction mixture was cooled to room temperature and filtered. The filtrate was concentrated under vacuum. The residue was dissolved in 2 L of EtOH, then a solution of oxalic acid in EtOH was added and stirred for 1 hour. The solid was collected by filtration and washed with ethanol. This afforded ethyl 3-aza-bicyclo [3.1.0]hexane-6-carboxylate.

Step E: 3-tert-butyl 6-ethyl 3-aza-bicyclo[3.1.0]hexane-3,6-dicarboxylate

Into a 100-mL 3-necked round-bottom flask was placed a solution of ethyl 3-aza-bicyclo[3.1.0]hexane-6-carboxylate oxalate (1.3 g, 5.31 mmol, 1.00 equiv.) in 20 mL water at room temperature, then a solution of sodium carbonate (1.68 g, 15.85 mmol, 3.00 equiv.) in 20 mL water was added dropwise with stirring at room temperature over 5 minutes. This was followed by the addition of a solution of (Boc)$_2$O (1.62 g, 7.43 mmol, 1.40 equiv) in 30 mL THF at room temperature. The resulting solution was stirred for 0.5 hours at room temperature, then concentrated under vacuum. The residual solution was diluted with 30 mL of water, then extracted with 3×20 mL of ethyl acetate. The organic layers were combined, dried over anhydrous sodium sulfate and concentrated under vacuum. This afforded 3-tert-butyl 6-ethyl 3-aza-bicyclo[3.1.0]hexane-3,6-dicarboxylate. LC-MS (ES, m/z): 241 [M+H-(Bu-t)+MeCN]$^+$. This compound was determined to be the trans-isomer by 1H-1H 2D NOE (NOESY) spectrum.

Step F: 3-(tert-butoxycarbonyl)-3-aza-bicyclo[3.1.0]hexane-6-carboxylic acid Into a 5000-mL 4-necked round-bottom flask was placed a solution of 3-tert-butyl 6-ethyl 3-aza-bicyclo[3.1.0]hexane-3,6-dicarboxylate (580 g, 1.82 mol, 1.00 equiv., 80%) in 2000 mL ethanol at room temperature. This was followed by the addition of a solution of sodium hydroxide (171.43 g, 4.29 mol, 2.50 equiv.) in 1000 mL water dropwise with stirring at 10° C. over 30 minutes. The resulting solution was stirred for 1 hour at room temperature, then concentrated under vacuum. The residue was diluted with 1000 mL of water, then washed with 3×500 mL of dichloromethane. The aqueous layer was adjusted to pH 1 with sulfuric acid (20%). The resulting solution was extracted with 4×1000 mL of ethyl acetate. The organic layers were combined, dried over anhydrous sodium sulfate and concentrated under vacuum. The resulting material was washed with 4×500 mL of water and 4×500 mL of n-hexane. This afforded the title compound. LC-MS (ES, m/z): [M+H-(Bu-t)+MeCN]$^+$. H-NMR (400 MHz, DMSO-d6, ppm): 1.23-1.24(1H, t), 1.37(9H, s), 1.96-1.97(2H, t), 3.29-3.35(2H, s), 3.47-3.49(2H, d).

EXAMPLE 1

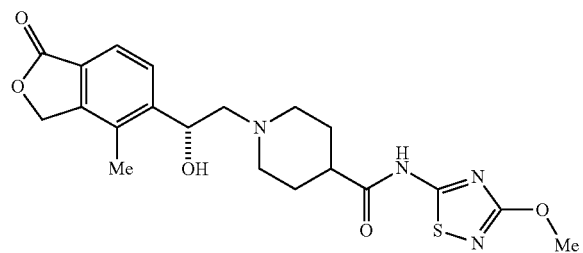 [SMILES: COc1nsc(NC(=O)C2CCN(C[C@H](O)c3ccc4c(c3C)COC4=O)CC2)n1]

(R)-1-(2-Hydroxy-2-(4-methyl-1-oxo-1,3-dihydroisobenzofuran-5-yl)ethyl)-N-(3-methoxy-1,2,4-thiadiazol-5-yl)piperidine-4-carboxamide To a flask charged with (R)-1-(2-hydroxy-2-(4-methyl-1-oxo-1,3-dihydroisobenzofuran-5-yl)ethyl)piperidine-4-carboxylic acid (150 mg, 0.47 mmol), 3-methoxy-1,2,4-thiadiazol-5-amine (74 mg, 0.56 mmol), HATU (210 mg, 0.56 mmol) and a stir bar was added DMF (10 mL) and triethylamine (0.14 mL, 0.94 mmol). The mixture was allowed to stir for 16 hours at RT. The reaction was diluted with water, and extracted with EtOAc. The extractions were combined, washed with brine, filtered and concentrated. The crude material was separated by reverse phase HPLC. LCMS: 433 (M+H)$^+$.

EXAMPLE 2

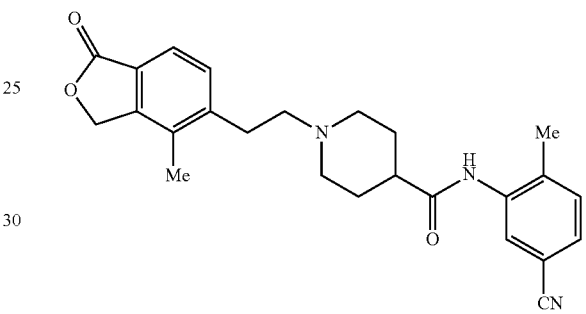

N-(5-cyano-2-methylphenyl)-1-(2-(4-methyl-1-oxo-1,3-dihydroisobenzofuran-5-yl)ethyl)piperidine-4-carboxamide A solution of 1-(2-(4-methyl-1-oxo-1,3-dihydroisobenzofuran-5-yl)ethyl)piperidine-4-carboxylic acid (30 mg, 0.10 mmol) in SOCl$_2$ (2 mL) was stirred at 120° C. for 2 h. The solution was cooled and concentrated in vacuum to give 1-(2-(4-methyl-1-oxo-1,3-dihydroisobenzofuran-5-yl)ethyl)piperidine-4-carbonyl chloride. The acid chloride was combined with 3-amino-4-methylbenzonitrile (15 mg, 0.100 mmol), TEA (30 mg, 0.300 mmol) in DCM (2 mL) and was stirred at r.t. for 2 h. The mixture was concentrated and purified by HPLC to afford the title compound. LC-MS: 417 (M+H)$^+$.

The following two compounds in Table 1 were made in a similar fashion as described for N-(5-cyano-2-methylphenyl)-1-(2-(4-methyl-1-oxo-1,3-dihydroisobenzofuran-5-yl)ethyl)piperidine-4-carboxamide (Example 2) starting with 1-(2-(4-methyl-1-oxo-1,3-dihydroisobenzofuran-5-yl)ethyl)piperidine-4-carboxylic acid and using the indicated amines as coupling partners.

TABLE 1

| Example | Amine | Structure | LC-MS |
|---|---|---|---|
| 3 | | 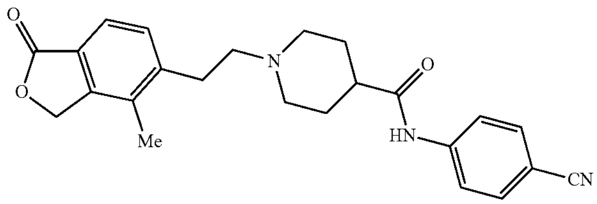 [SMILES: Cc1c(CCN2CCC(C(=O)Nc3ccc(C#N)cc3)CC2)ccc2c1COC2=O] | 403 (M + H)+ |
| | | N-(4-cyanophenyl)-1-(2-(4-methyl-1-oxo-1,3-dihydroisobenzofuran-5-yl)ethyl)piperidine-4-carboxamide | |
| 4 | | 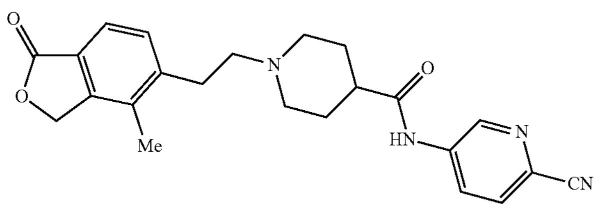 [SMILES: Cc1c(CCN2CCC(C(=O)Nc3ccc(C#N)nc3)CC2)ccc2c1COC2=O] | 404 (M + H)+ |
| | | N-(6-cyanopyridin-3-yl)-1-(2-(4-methyl-1-oxo-1,3-dihydroisobenzofuran-5-yl)ethyl)piperidine-4-carboxamide | |

EXAMPLE 5

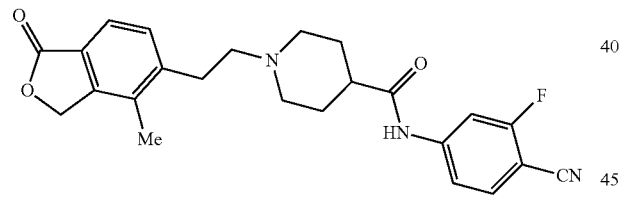

N-(4-cyano-3-fluorophenyl)-1-(2-(4-methyl-1-oxo-1,3-dihydroisobenzofuran-5-yl)ethyl)piperidine-4-carboxamide Step A: 1-(2-(4-methyl-1-oxo-1,3-dihydroisobenzofuran-5-yl)ethyl)piperidine-4-carboxamide A solution of 1-(2-(4-methyl-1-oxo-1,3-dihydroisobenzofuran-5-yl)ethyl)piperidine-4-carboxylic acid (60 mg, 0.200 mmol) in $SOCl_2$ (5 mL) was stirred at 120° C. for 2 h. The solution was cooled and concentrated in vacuum to give 1-(2-(4-methyl-1-oxo-1,3-dihydroisobenzofuran-5-yl)ethyl)piperidine-4-carbonyl chloride. To the acid chloride in THF (5 mL) was added $NH_3.H_2O$ (2 mL) dropwise at −15° C. and the mixture was stirred for 0.5 h. The reaction mixture was poured into a separating funnel and separated. The organic layer was washed with brine, dried with $MgSO_4$, filtered and concentrated in vacuo. The residue was purified by preparative-TLC to afford title compound.

Step B: N-(4-cyano-3-fluorophenyl)-1-(2-(4-methyl-1-oxo-1,3-dihydroisobenzofuran-5-yl)ethyl)piperidine-4-carboxamide A mixture of 1-(2-(4-methyl-1-oxo-1,3-dihydroisobenzofuran-5-yl)ethyl)piperidine-4-carboxamide (13 mg, 0.043 mmol), 4-bromo-2-fluorobenzonitrile (9 mg, 0.043 mmol), $Pd_2(dba)_3$ (1 mg, 0.0009 mmol), Xantphos (1 mg, 0.002 mmol), $Cs_2CO_3$ (28 mg, 0.086 mmol) in dioxane (5 mL) was stirred at 100° C. for 16 h under $N_2$. After cooling to r.t., the mixture was concentrated in vacuo and purified by HPLC to afford the title compound. LC-MS: 421 (M+H)+.

The following compounds in Table 2 were made in a similar fashion as described for N-(4-cyano-3-fluorophenyl)-1-(2-(4-methyl-1-oxo-1,3-dihydroisobenzofuran-5-yl)ethyl)piperidine-4-carboxamide (Example 5) starting with 1-(2-(4-methyl-1-oxo-1,3-dihydroisobenzofuran-5-yl)ethyl)piperidine-4-carboxylic acid and using the indicated bromides as coupling partners.

TABLE 2

| Example | Bromide | Structure | LC-MS |
|---|---|---|---|
| 6 | 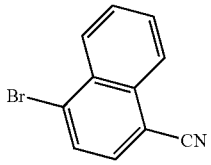 [SMILES: N#Cc1ccc(Br)c2ccccc12] | 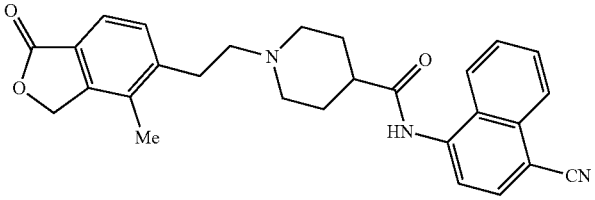 [SMILES: Cc1c(CCN2CCC(C(=O)Nc3ccc(C#N)c4ccccc34)CC2)ccc2c1COC2=O]<br>N-(4-cyanonaphthalen-1-yl)-1-(2-(4-methyl-1-oxo-1,3-dihydroisobenzofuran-5-yl)ethyl)piperidine-4-carboxamide | 453 (M + H)+ |
| 7 | 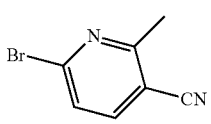 | 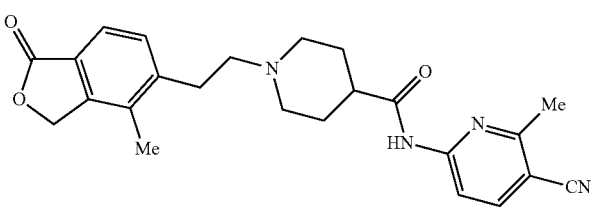 [SMILES: Cc1nc(NC(=O)C2CCN(CCc3ccc4c(c3C)COC4=O)CC2)ccc1C#N]<br>N-(5-cyano-6-methylpyridin-2-yl)-1-(2-(4-methyl-1-oxo-1,3-dihydroisobenzofuran-5-yl)ethyl)piperidine-4-carboxamide | 418 (M + H)+ |
| 8 | 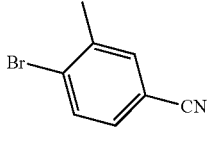 | 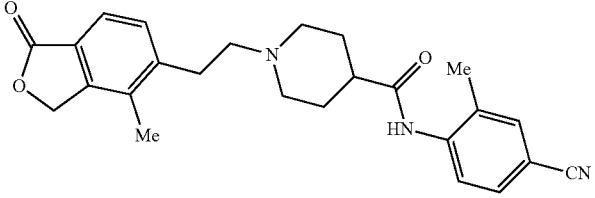 [SMILES: Cc1cc(C#N)ccc1NC(=O)C1CCN(CCc2ccc3c(c2C)COC3=O)CC1]<br>N-(4-cyano-2-methylphenyl)-1-(2-(4-methyl-1-oxo-1,3-dihydroisobenzofuran-5-yl)ethyl)piperidine-4-carboxamide | 417 (M + H)+ |
| 9 | 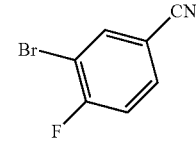 | 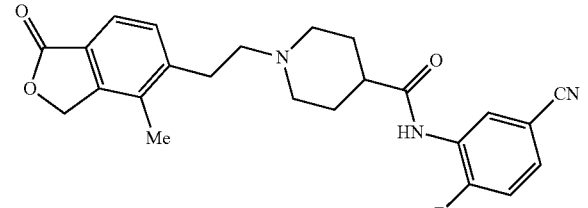<br>N-(5-cyano-2-fluorophenyl)-1-(2-(4-methyl-1-oxo-1,3-dihydroisobenzofuran-5-yl)ethyl)piperidine-4-carboxamide | 421 (M + H)+ |
| 10 | 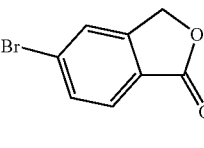 | 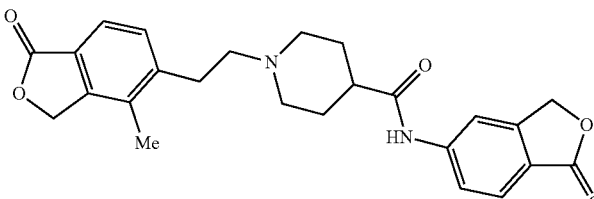<br>1-(2-(4-methyl-1-oxo-1,3-dihydroisobenzofuran-5-yl)ethyl)-N-(1-oxo-1,3-dihydroisobenzofuran-5-yl)piperidine-4-carboxamide | 434 (M + H)+ |

TABLE 2-continued

| Example | Bromide | Structure | LC-MS |
|---|---|---|---|
| 11 | (Br-benzoxadiazole) | N-(benzo[c][1,2,5]oxadiazol-5-yl)-1-(2-(4-methyl-1-oxo-1,3-dihydroisobenzofuran-5-yl)ethyl)piperidine-4-carboxamide | 420 (M + H)+ |

EXAMPLE 12

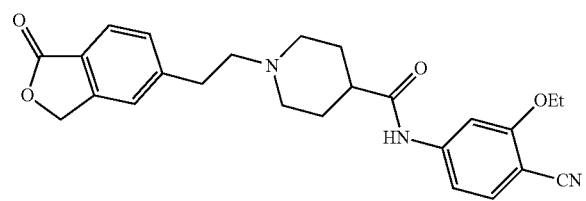 [SMILES: COc1cc(NC(=O)C2CCN(CCc3ccc4c(c3)COC4=O)CC2)ccc1C#N]

N-(4-cyano-3-ethoxyphenyl)-1-[2-(1-oxo-1,3-dihydro-2-benzofuran-5-yl)ethyl]piperidine-4-carboxamide 1-(2-(1-oxo-1,3-dihydroisobenzofuran-5-yl)ethyl)piperidine-4-carboxylic acid (30 mg, 0.104 mmol) and 4-amino-2-ethoxybenzonitrile (19.5 mg, 0.12 mmole) in 0.4 mL of DMF was added to a 4 mL vial. Next propylphosphonic anhydride solution (50% wt in ethyl acetate, 0.132 mL, 0.221 mmol) and diisopropyl ethylamine (91 uL) were added. The mixture was stirred at room temperature overnight and the reaction was monitored by LCMS. After completion of the reaction, ethyl acetate was removed and the mixture was diluted with 1 mL of DMSO. The crude product was then purified by reverse phase mass directed HPLC purification system to give the title product. Mass directed reverse phase prep LCMS method: Waters XBridge C18, 5 u, 30×100 mm, mobile phase A=Water+0.1% Ammonium Hydroxide, mobile phase B=MeCN+0.1% Ammonium Hydroxide, Gradient from 35 to 85% MeCN, 70 ml/min flow rate, run time 8 minutes. Analytical UPLC method: Waters Acquity UPLC, BEH C18 1.7 um, 2.1×50 mm, MeCN and water with 0.1% ammonium hydroxide as solvents. 1 mL/min flow rate, gradient 5%-100% MeCN over 1.4 min. LC/MS: (IE, m/z) [(M+1)]+= 434.45.

The following compounds in Table 3 were made in a similar fashion as described for N-(4-cyano-3-ethoxyphenyl)-1-[2-(1-oxo-1,3-dihydro-2-benzofuran-5-yl)ethyl]piperidine-4-carboxamide (Example 12) starting with 1-(2-(1-oxo-1,3-dihydroisobenzofuran-5-yl)ethyl)piperidine-4-carboxylic acid and using the indicated amines as coupling partners.

TABLE 3

| Example | Amine | Structure | LC-MS |
|---|---|---|---|
| 13 | (H2N-phenyl-OMe, CN) | N-(4-cyano-3-methoxyphenyl)-1-(2-(1-oxo-1,3-dihydroisobenzofuran-5-yl)ethyl)piperidine-4-carboxamide | 420 (M + H)+ |

TABLE 3-continued

| Example | Amine | Structure | LC-MS |
|---|---|---|---|
| 14 | 4-amino-2,5-difluorobenzonitrile | N-(4-cyano-2,5-difluorophenyl)-1-(2-(1-oxo-1,3-dihydroisobenzofuran-5-yl)ethyl)piperidine-4-carboxamide | 426 (M + H)⁺ |
| 15 | 4-amino-3-(trifluoromethoxy)benzonitrile | N-(4-cyano-2-(trifluoromethoxy)phenyl)-1-(2-(1-oxo-1,3-dihydroisobenzofuran-5-yl)ethyl)piperidine-4-carboxamide | 474 (M + H)⁺ |
| 16 | 5-amino-2-chlorobenzonitrile | N-(4-chloro-3-cyanophenyl)-1-(2-(1-oxo-1,3-dihydroisobenzofuran-5-yl)ethyl)piperidine-4-carboxamide | 424 (M + H)⁺ |
| 17 | 5-amino-2-fluorobenzonitrile | N-(3-cyano-4-fluorophenyl)-1-(2-(1-oxo-1,3-dihydroisobenzofuran-5-yl)ethyl)piperidine-4-carboxamide | 408 (M + H)⁺ |
| 18 | 1H-indazol-6-amine | N-(1H-indazol-6-yl)-1-(2-(1-oxo-1,3-dihydroisobenzofuran-5-yl)ethyl)piperidine-4-carboxamide | 405 (M + H)⁺ |

Note: LC-MS values are shown as $(M + H)^+$.

TABLE 3-continued

| Example | Amine | Structure | LC-MS |
|---|---|---|---|
| 19 | H₂N-benzotriazole structure | N-(1H-benzo[d][1,2,3]triazol-5-yl)-1-(2-(1-oxo-1,3-dihydroisobenzofuran-5-yl)ethyl)piperidine-4-carboxamide | 406 (M + H)⁺ |
| 20 | H₂N-benzisothiazole structure | N-(benzo[d]isothiazol-5-yl)-1-(2-(1-oxo-1,3-dihydroisobenzofuran-5-yl)ethyl)piperidine-4-carboxamide | 422 (M + H)⁺ |
| 21 | H₂N-pyrrole-CN with 4-fluorophenyl | N-(4-cyano-1-(4-fluorophenyl)-1H-pyrrol-2-yl)-1-(2-(1-oxo-1,3-dihydroisobenzofuran-5-yl)ethyl)piperidine-4-carboxamide | 473 (M + H)⁺ |

EXAMPLE 22

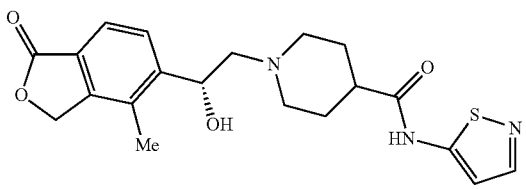 [SMILES: Cc1c([C@@H](O)CN2CCC(C(=O)Nc3ccns3)CC2)ccc2c1COC2=O]

1-[(2R)-2-hydroxy-2-(4-methyl-1-oxo-1,3-dihydro-2-benzofuran-5-yl)ethyl]-N-(isothiazol-5-yl)piperidine-4-carboxamide To a 1 dram, 4 mL vial containing 1 mL of N,N dimethylacetamide was added (R)-1-(2-hydroxy-2-(4-methyl-1-oxo-1,3-dihydroisobenzofuran-5-yl)ethyl)piperidine-4-carboxylic acid (0.036 g, 0.113 mmol), HBTU (0.064 g, 0.169 mmol), isothiazol-5-amine (0.017 g, 00169 mmol), and diisopropyl ethylamine (0.056 mL, 0.2338 mmol). The vial was placed on an orbital shaker at room temperature and agitated for 16 hours. The reaction was analyzed by LC/MS where the reaction was deemed complete. The solution was filtered and purified by semi-preparative reverse phase HPLC and the fractions containing the desired product were lyophilized to dryness to obtain the title compound. LC/MS: (IE, m/z) [(M+1)]⁺=402.3. ¹H NMR (500 MHz, CD₃OD) δ 1.30 (m, 2H), 1.36 (m, 2H), 1.85-2.0 (b.s., 2H), 2.35 (s, 3H), 2.40 (m, 1H), 2.52-2.72 (m, 1H), 3.25-3.30 (m, 1H), 3.67 (d, 2H), 5.28 (t, 1H), 5.38 (s, 2H), 6.91 (d, 1H), 7.71-7.81 (dd, 2H), 8.21 (d, 1H).

The following compounds in Table 4 were made in a similar fashion as described for 1-[(2R)-2-hydroxy-2-(4-methyl-1-oxo-1,3-dihydro-2-benzofuran-5-yl)ethyl]-N-(isothiazol-5-yl)piperidine-4-carboxamide (Example 22) starting with (R)-1-(2-hydroxy-2-(4-methyl-1-oxo-1,3-dihydroisobenzofuran-5-yl)ethyl)piperidine-4-carboxylic acid and using the indicated commercially available or known amines as coupling partners.

TABLE 4

| EXAMPLE | Amine | Structure | LC-MS |
|---|---|---|---|
| 23 | 4-(1H-pyrazol-1-yl)aniline | (R)-N-(4-(1H-pyrazol-1-yl)phenyl)-1-(2-hydroxy-2-(4-methyl-1-oxo-1,3-dihydroisobenzofuran-5-yl)ethyl)piperidine-4-carboxamide | 461 (M + H)+ |
| 24 | 3-(1H-tetrazol-1-yl)aniline | (R)-N-(3-(1H-tetrazol-1-yl)phenyl)-1-(2-hydroxy-2-(4-methyl-1-oxo-1,3-dihydroisobenzofuran-5-yl)ethyl)piperidine-4-carboxamide | 463 (M + H)+ |
| 25 | 4-amino-2-ethoxybenzonitrile | (R)-N-(4-cyano-3-ethoxyphenyl)-1-(2-hydroxy-2-(4-methyl-1-oxo-1,3-dihydroisobenzofuran-5-yl)ethyl)piperidine-4-carboxamide | 464 (M + H)+ |
| 26 | 4-amino-2-methoxybenzonitrile | (R)-N-(4-cyano-3-methoxyphenyl)-1-(2-hydroxy-2-(4-methyl-1-oxo-1,3-dihydroisobenzofuran-5-yl)ethyl)piperidine-4-carboxamide | 450 (M + H)+ |
| 27 | isoxazol-4-amine | (R)-1-(2-hydroxy-2-(4-methyl-1-oxo-1,3-dihydroisobenzofuran-5-yl)ethyl)-N-(isoxazol-4-yl)piperidine-4-carboxamide | 386 (M + H)+ |

TABLE 4-continued

| EXAMPLE | Amine | Structure | LC-MS |
|---|---|---|---|
| 28 | isothiazol-4-amine | (R)-1-(2-hydroxy-2-(4-methyl-1-oxo-1,3-dihydroisobenzofuran-5-yl)ethyl)-N-(isothiazol-4-yl)piperidine-4-carboxamide | 403 (M + H)+ |
| 29 | 2-aminothiazole-4-carbonitrile | (R)-N-(4-cyanothiazol-2-yl)-1-(2-hydroxy-2-(4-methyl-1-oxo-1,3-dihydroisobenzofuran-5-yl)ethyl)piperidine-4-carboxamide | 427 (M + H)+ |
| 30 | isothiazolo[4,3-c]pyridin-3-amine | (R)-1-(2-hydroxy-2-(4-methyl-1-oxo-1,3-dihydroisobenzofuran-5-yl)ethyl)-N-(isothiazolo[4,3-c]pyridin-3-yl)piperidine-4-carboxamide | 453 (M + H)+ |
| 31 | 3-methyl-1,2,4-thiadiazol-5-amine | (R)-1-(2-hydroxy-2-(4-methyl-1-oxo-1,3-dihydroisobenzofuran-5-yl)ethyl)-N-(3-methyl-1,2,4-thiadiazol-5-yl)piperidine-4-carboxamide | 417 (M + H)+ |
| 32 | 3-cyclopropyl-1,2,4-thiadiazol-5-amine | (R)-N-(3-cyclopropyl-1,2,4-thiadiazol-5-yl)-1-(2-hydroxy-2-(4-methyl-1-oxo-1,3-dihydroisobenzofuran-5-yl)ethyl)piperidine-4-carboxamide | 443 (M + H)+ |

TABLE 4-continued

| EXAMPLE | Amine | Structure | LC-MS |
|---|---|---|---|
| 33 | 4-(1,2,3-thiadiazol-4-yl)aniline | (R)-N-(4-(1,2,3-thiadiazol-4-yl)phenyl)-1-(2-hydroxy-2-(4-methyl-1-oxo-1,3-dihydroisobenzofuran-5-yl)ethyl)piperidine-4-carboxamide | 479 (M + H)+ |
| 34 | 5-fluoropyridin-3-amine | (R)-N-(5-fluoropyridin-3-yl)-1-(2-hydroxy-2-(4-methyl-1-oxo-1,3-dihydroisobenzofuran-5-yl)ethyl)piperidine-4-carboxamide | 414 (M + H)+ |
| 35 | pyridin-4-amine | (R)-1-(2-hydroxy-2-(4-methyl-1-oxo-1,3-dihydroisobenzofuran-5-yl)ethyl)-N-(pyridin-4-yl)piperidine-4-carboxamide | 396 (M + H)+ |
| 36 | 3-methylisothiazol-5-amine | (R)-1-(2-hydroxy-2-(4-methyl-1-oxo-1,3-dihydroisobenzofuran-5-yl)ethyl)-N-(3-methylisothiazol-5-yl)piperidine-4-carboxamide | 416 (M + H)+ |

EXAMPLE 37

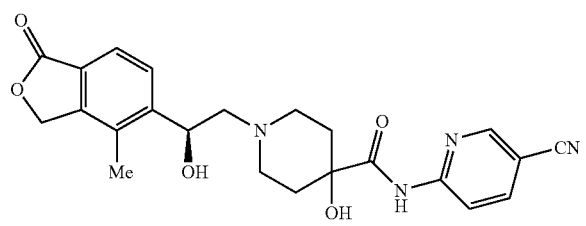 [SMILES: Cc1c([C@H](O)CN2CCC(O)(C(=O)Nc3ccc(C#N)cn3)CC2)ccc2c1COC2=O]

(R)-N-(5-cyanopyridin-2-yl)-4-hydroxy-1-(2-hydroxy-2-(4-methyl-1-oxo-1,3-dihydroisobenzofuran-5-yl)ethyl)piperidine-4-carboxamide Step A: tert-butyl 4-((5-cyanopyridin-2-yl)carbamoyl)-4-hydroxypiperidine-1-carboxylate 1-(tert-Butoxycarbonyl)-4-hydroxypiperidine-4-carboxylic acid (100 mg, 0.408 mmol) and 6-aminonicotinonitrile (48.6 mg, 0.408 mmol) were mixed in DMF (2 mL). DIEA (105 mg, 0.815 mmol) was added to this solution followed by HATU (233 mg, 0.612 mmol). The reaction mixture was stirred at room temperature for 12 hours. The product was purified by reverse phase prep-HPLC (10-90% AcCN/H2O+

0.1 TFA). The correct fractions were combined and concentrated to give the title compound. LC/MS: [(M+23)]⁺=369.0

Step B: (R)-N-(5-cyanopyridin-2-yl)-4-hydroxy-1-(2-hydroxy-2-(4-methyl-1-oxo-1,3-dihydroisobenzofuran-5-yl)ethyl)piperidine-4-carboxamide tert-Butyl 4-((5-cyanopyridin-2-yl)carbamoyl)-4-hydroxypiperidine-1-carboxylate (21 mg, 0.061 mmol) was treated with TFA in DCM for half an hour. The reaction mixture was then concentrated to remove excess of reagent and solvent. The resulting oil was dissolved in ethanol (2 ml), and DIEA (42.4 ul, 0.243 mmol) was added followed by (R)-4-methyl-5-(oxiran-2-yl)isobenzofuran-1(3H)-one (23.1 mg, 0.121 mmol). The reaction mixture was heated at 140° C. for 45 minutes in a microwave reactor. The solvent was then removed under reduced pressure and the residue was purified by preparative TLC to give the title compound. LC/MS: [(M+1)]⁺=437.03.

The following compounds in Table 5 were made in a similar fashion as described for (R)-N-(5-cyanopyridin-2-yl)-4-hydroxy-1-(2-hydroxy-2-(4-methyl-1-oxo-1,3-dihydroisobenzofuran-5-yl)ethyl)piperidine-4-carboxamide (Example 37) starting with 1-(tert-butoxycarbonyl)-4-hydroxypiperidine-4-carboxylic acid.

TABLE 5

| EXAMPLE | Structure | LC-MS |
|---------|-----------|-------|
| 38 | 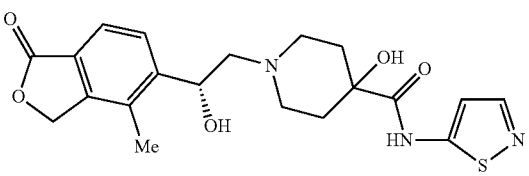 [SMILES: Cc1c([C@@H](O)CN2CCC(O)(C(=O)Nc3ccns3)CC2)ccc2c1COC2=O] (R)-4-hydroxy-1-(2-hydroxy-2-(4-methyl-1-oxo-1,3-dihydroisobenzofuran-5-yl)ethyl)-N-(isothiazol-5-yl)piperidine-4-carboxamide | 418 (M + H)⁺ |
| 39 | 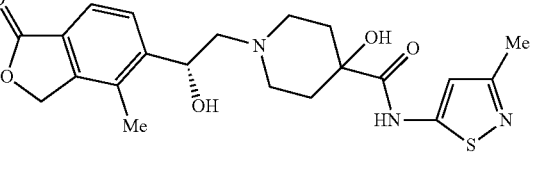 (R)-4-hydroxy-1-(2-hydroxy-2-(4-methyl-1-oxo-1,3-dihydroisobenzofuran-5-yl)ethyl)-N-(3-methylisothiazol-5-yl)piperidine-4-carboxamide | 432 (M + H)⁺ |
| 40 | 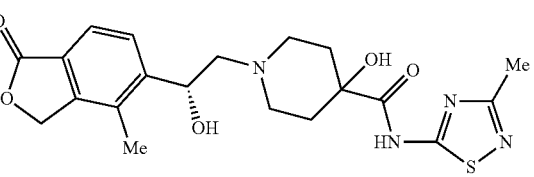 (R)-4-hydroxy-1-(2-hydroxy-2-(4-methyl-1-oxo-1,3-dihydroisobenzofuran-5-yl)ethyl)-N-(3-methyl-1,2,4-thiadiazol-5-yl)piperidine-4-carboxamide | 433 (M + H)⁺ |

EXAMPLE 41

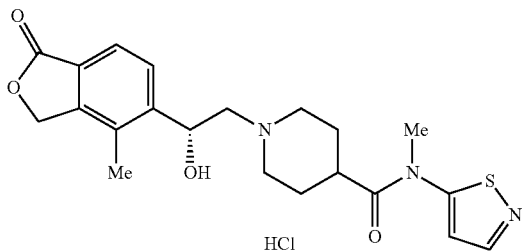 [SMILES: Cc1c([C@@H](O)CN2CCC(C(=O)N(C)c3ccns3)CC2)ccc2c1COC2=O ; Cl]

1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide and the hydrochloride salt thereof

Step A: tert-butyl 4-(isothiazol-5-ylcarbamoyl)piperidine-1-carboxylate

The title compound was prepared in the same manner as tert-butyl 4-((5-cyanopyridin-2-yl)carbamoyl)-4-hydroxypiperidine-1-carboxylate (see Example 37, Step A) starting from 1-(tert-butoxycarbonyl)piperidine-4-carboxylic acid and isothiazol-5-amine.

Step B: tert-butyl 4-[isothiazol-5-yl(methyl)carbamoyl]piperidine-1-carboxylate To an ice cooled solution of sodium hydride (16.8 mg, 1.05 mmol, 3 mL DMF) was added tert-butyl 4-(isothiazol-5-ylcarbamoyl)piperidine-1-carboxylate (125 mg, 0.401 mmol, 3 mL DMF). After 30 minutes, iodomethane (26 µL, 0.401 mmol) was added and the reaction was allowed to warm to ambient temperature. Upon completion, the reaction mixture was quenched with water and the aqueous layer was extracted with ethyl acetate (3×10 mL). The combined organic layers were then dried over sodium sulfate, filtered and concentrated in vacuo. The crude residue was purified via MPLC (0-100% EtOAc/Hex gradient) to afford tert-butyl 4-[isothiazol-5-yl(methyl)carbamoyl]piperidine-1-carboxylate. LC-MS (M+H)⁺326.

Step C: N-(isothiazol-5-yl)-N-methyl-3-azabicyclo[3.1.0]hexane-6-carboxamide hydrochloride To a solution of tert-butyl 4-[isothiazol-5-yl(methyl)carbamoyl]piperidine-1-carboxylate in MeOH was added an excess amount of 4 N HCl in dioxane solution. After addition, the reaction was allowed to stir at ambient temperature for one hour and then concentrated in vacuo to afford the title compound, which was used without further purification.

Step D: 1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide hydrochloride N-(isothiazol-5-yl)-N-methyl-3-azabicyclo[3.1.0]hexane-6-carboxamide hydrochloride was diluted in EtOH and treated with triethylamine (5 equivalents) for 10 minutes. After 10 minutes, 4-methyl-5-[(2R)-oxiran-2-yl]-2-benzofuran-1(3H)-one (1 equivalent) was added and the reaction mixture was heated to reflux for 15 hours. Once cooled, the reaction was concentrated in vacuo, then purified via preperative TLC to afford the title compound as its free base. The free base was then treated with excess 1N HCl in Et₂O solution to afford the HCl salt of the title compound after removal of solvents under vacuum. LC-MS (M+H)⁺416.

The following compounds in Table 6 were made in a similar fashion as described for 1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide (free base) and its hydrochloride salt (Example 41), starting with 1-(tert-butoxycarbonyl)piperidine-4-carboxylic acid using the indicated commercially available or known amines as coupling partners, and alkylation of the secondary amides with iodomethane or other alkyl halides. In some cases the free bases were isolated and in others the free bases were subsequently converted to their corresponding hydrochloride salts.

TABLE 6

| EXAMPLE | Structure | LC-MS |
|---|---|---|
| 42 | 1-[(2R)-2-hydroxy-2-(4-methyl-1-oxo-1,3-dihydro-2-benzofuran-5-yl)ethyl]-N-(isothiazol-5-yl)-N-trideuteromethylpiperidine-4-carboxamide and the hydrochloride salt thereof | 419 (M + H)⁺ |

TABLE 6-continued

| EXAMPLE | Structure | LC-MS |
|---|---|---|
| 43 | (R)-N-ethyl-1-(2-hydroxy-2-(4-methyl-1-oxo-1,3-dihydroisobenzofuran-5-yl)ethyl)-N-(isothiazol-5-yl)piperidine-4-carboxamide | 430 (M + H)⁺ |
| 44 | (R)-1-(2-hydroxy-2-(4-methyl-1-oxo-1,3-dihydroisobenzofuran-5-yl)ethyl)-N-methyl-N-(3-methylisothiazol-5-yl)piperidine-4-carboxamide | 430 (M + H)⁺ |
| 45 | (R)-1-(2-hydroxy-2-(4-methyl-1-oxo-1,3-dihydroisobenzofuran-5-yl)ethyl)-N-(3-methoxy-1,2,4-thiadiazol-5-yl)-N-methylpiperidine-4-carboxamide | 447 (M + H)⁺ |

EXAMPLE 46

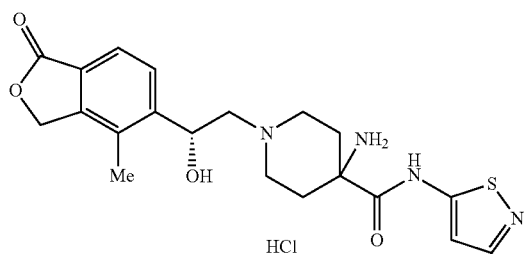 [SMILES: Cc1c([C@@H](O)CN2CCC(N)(C(=O)Nc3ccns3)CC2)ccc2c1COC2=O ; Cl]

4-amino-1-[(2R)-2-hydroxy-2-(4-methyl-1-oxo-1,3-dihydro-2-benzofuran-5-yl)ethyl]-N-(isothiazol-5-yl)piperidine-4-carboxamide hydrochloride Step A: methyl 4-[(tert-butoxycarbonyl)amino]-1-[(2R)-2-hydroxy-2-(4-methyl-1-oxo-1,3-dihydro-2-benzofuran-5-yl)ethyl]piperidine-4-carboxylate Methyl 4-[(tert-butoxycarbonyl)amino]piperidine-4-carboxylate (500 mg, 1.94 mmol) and 4-methyl-5-[(2R)-oxiran-2-yl]-2-benzofuran-1(3H)-one (552 mg, 2.90 mmol) were diluted in EtOH (5 mL) and the reaction mixture was heated to reflux for 15 hours. Once cooled, the reaction was concentrated in vacuo, then purified via MPLC (0-100% EtOAc/Hex gradient) to afford the title compound. LC-MS (M+H)⁺ 449.

Step B: 4-[(tert-butoxycarbonyl)amino]-1-[(2R)-2-hydroxy-2-(4-methyl-1-oxo-1,3-dihydro-2-benzofuran-5-yl)ethyl]piperidine-4-carboxylic acid To an ice-cooled solution of methyl 4-[(tert-butoxycarbonyl)amino]-1-[(2R)-2-hydroxy-2-(4-methyl-1-oxo-1,3-dihydro-2-benzofuran-5-yl)ethyl]piperidine-4-carboxylate (560 mg, 1.25 mmol, 6 mL THF) was added potassium trimethylsilanolate (481 mg, 3.75 mmol). The reaction was allowed to warm to ambient temperature gradually overnight. After overnight stirring, the reaction mixture was concentrated in vacuo to afford the title compound, which was used without further purification.

Step C: tert-butyl {1-[(2R)-2-hydroxy-2-(4-methyl-1-oxo-1,3-dihydro-2-benzofuran-5-yl)ethyl]-4-(isothiazol-5-ylcarbamoyl)piperidin-4-yl}carbamate The title compound was prepared in the same manner as tert-butyl 4-((5-cyanopyridin-2-yl)carbamoyl)-4-hydroxypiperidine-1-carboxylate (see Example 37), using HATU as the coupling reagent. LC-MS (M+H)$^+$ 517.

Step D: 4-amino-1-[(2R)-2-hydroxy-2-(4-methyl-1-oxo-1,3-dihydro-2-benzofuran-5-yl)ethyl]-N-(isothiazol-5-yl)piperidine-4-carboxamide hydrochloride To a solution of tert-butyl {1-[(2R)-2-hydroxy-2-(4-methyl-1-oxo-1,3-dihydro-2-benzofuran-5-yl)ethyl]-4-(isothiazol-5-ylcarbamoyl)piperidin-4-yl}carbamate in MeOH was added an excess amount of a 4 N HCl in dioxane solution. After addition, the reaction was allowed to stir at ambient temperature for one hour and then concentrated in vacuo to afford the title compound as an HCl salt. LC-MS (M+H)$^+$417.

EXAMPLE 47

4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide and the hydrochloride salt thereof Step A: tert-butyl 4-fluoro-4-(isothiazol-5-ylcarbamoyl)piperidine-1-carboxylate The title compound was prepared in the same manner as tert-butyl 4-((5-cyanopyridin-2-yl)carbamoyl)-4-hydroxypiperidine-1-carboxylate (see Example 37), using HATU as the coupling reagent and commercially available 1-(tert-butoxycarbonyl)-4-fluoropiperidine-4-carboxylic acid was used as the acid starting material.

Step B: 4-fluoro-N-(isothiazol-5-yl)piperidine-4-carboxamide hydrochloride

To a solution of tert-butyl 4-fluoro-4-(isothiazol-5-ylcarbamoyl)piperidine-1-carboxylate in MeOH was added an excess amount of a 4 N HCl in dioxane solution. After addition, the reaction was allowed to stir at ambient temperature for one hour and then concentrated in vacuo to afford the title compound.

Step C: 4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide hydrochloride The title compound was prepared in the same manner as 1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide hydrochloride (Example 41) starting from 4-fluoro-N-(isothiazol-5-yl)piperidine-4-carboxamide hydrochloride and 4-methyl-5-[(2R)-oxiran-2-yl]-2-benzofuran-1(3H)-one. LC-MS (M+H)$^+$ 366.

The following compounds in Table 7 were made in a similar fashion as described for 4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide hydrochloride (Example 47) starting with 1-(tert-butoxycarbonyl)-4-fluoropiperidine-4-carboxylic acid using commercially available or known amines as coupling partners.

TABLE 7

| EXAMPLE | Structure | LC-MS |
|---|---|---|
| 48 | 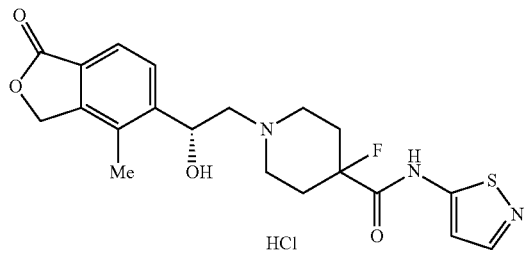 [SMILES: Cc1c([C@@H](O)CN2CCC(F)(C(=O)Nc3ccns3)CC2)ccc2c1COC2=O ; Cl] (R)-4-fluoro-1-(2-hydroxy-2-(4-methyl-1-oxo-1,3-dihydroisobenzofuran-5-yl)ethyl)-N-(3-methylisothiazol-5-yl)piperidine-4-carboxamide and the hydrochloride salt thereof | 434 (M + H)$^+$ |

TABLE 7-continued

| EXAMPLE | Structure | LC-MS |
|---|---|---|
| 49 | 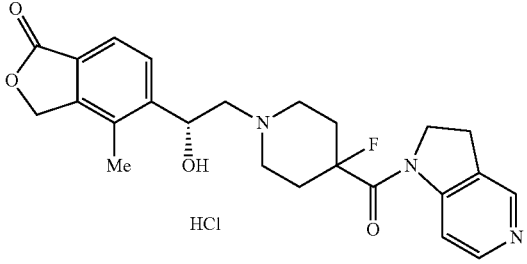 [SMILES: Cc1c([C@@H](O)CN2CCC(F)(C(=O)N3CCc4cnccc43)CC2)ccc2c1COC2=O ; Cl] (R)-5-(2-(4-(2,3-dihydro-1H-pyrrolo[3,2-c]pyridine-1-carbonyl)-4-fluoropiperidin-1-yl)-1-hydroxyethyl)-4-methylisobenzofuran-1(3H)-one and the hydrochloride salt thereof | 440 (M + H)+ |
| 50 | 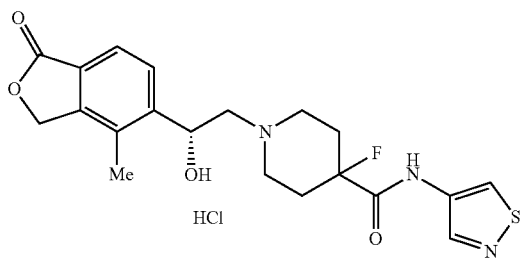 [SMILES: Cc1c([C@@H](O)CN2CCC(F)(C(=O)Nc3cnsc3)CC2)ccc2c1COC2=O ; Cl] (R)-4-fluoro-1-(2-hydroxy-2-(4-methyl-1-oxo-1,3-dihydroisobenzofuran-5-yl)ethyl)-N-(isothiazol-4-yl)piperidine-4-carboxamide and the hydrochloride thereof | 420 (M + H)+ |
| 51 | 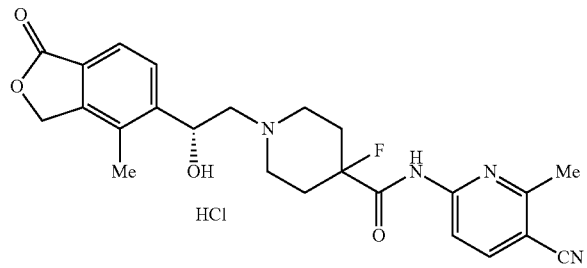 [SMILES: Cc1nc(NC(=O)C2(F)CCN(C[C@H](O)c3ccc4c(c3C)COC4=O)CC2)ccc1C#N ; Cl] (R)-N-(5-cyano-6-methylpyridin-2-yl)-4-fluoro-1-(2-hydroxy-2-(4-methyl-1-oxo-1,3-dihydroisobenzofuran-5-yl)ethyl)piperidine-4-carboxamide and the hydrochloride salt thereof | 453 (M + H)+ |
| 52 | 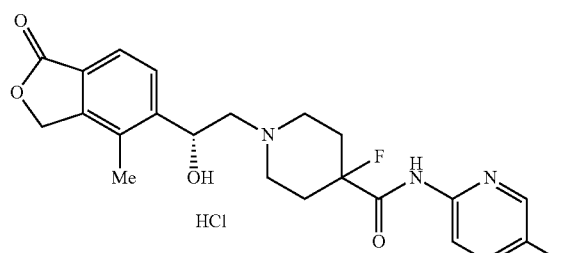 (R)-N-(5-cyanopyridin-2-yl)-4-fluoro-1-(2-hydroxy-2-(4-methyl-1-oxo-1,3-dihydroisobenzofuran-5-yl)ethyl)piperidine-4-carboxamide and the hydrochloride salt thereof | 439 (M + H)+ |

TABLE 7-continued

| EXAMPLE | Structure | LC-MS |
|---|---|---|
| 53 | 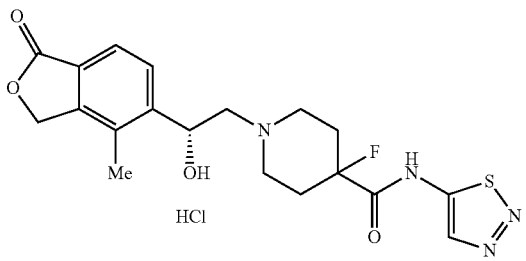 [SMILES: Cc1c([C@@H](O)CN2CCC(F)(C(=O)Nc3cnns3)CC2)ccc2c1COC2=O ; Cl]<br>(R)-4-fluoro-1-(2-hydroxy-2-(4-methyl-1-oxo-1,3-dihydroisobenzofuran-5-yl)ethyl)-N-(1,2,3-thiadiazol-5-yl)piperidine-4-carboxamide and the hydrochloride salt thereof | 421 (M + H)⁺ |

EXAMPLE 54

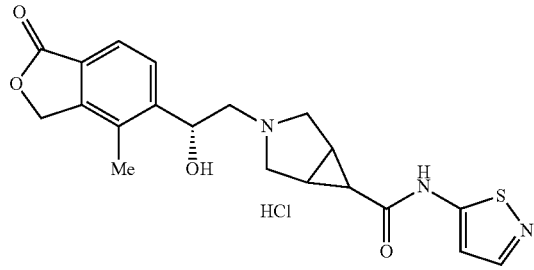 [SMILES: Cc1c([C@@H](O)CN2CC3C(C2)C3C(=O)Nc2ccns2)ccc2c1COC2=O ; Cl]

3-[(2R)-2-hydroxy-2-(4-methyl-1-oxo-1,3-dihydro-2-benzofuran-5-yl)ethyl]-N-(isothiazol-5-yl)-3-azabicyclo[3.1.0]hexane-6-carboxamide and the hydrochloride salt thereof

Step A: tert-butyl 6-(isothiazol-5-ylcarbamoyl)-3-azabicyclo[3.1.0]hexane-3-carboxylate To a solution of 3-(tert-butoxycarbonyl)-3-azabicyclo[3.1.0]hexane-6-carboxylic acid (182 mg, 0.799 mmol, 3 mL DMF) was added HATU. In a separate flask, triethylamine (390 µL, 2.80 mmol) was added to a solution of isothiazol-5-amine (80 mg, 0.799 mmol, 3 mL DMF). Both solutions were allowed to stir at ambient temperature for 15 minutes and then combined. After 2 hours, the reaction mixture was quenched with water and the aqueous layer was extracted with ethyl acetate (3×10 mL). The combined organic layers were then dried over sodium sulfate, filtered and concentrated in vacuo. The crude residue was purified via MPLC (0-100% EtOAc/Hex gradient) to afford the title compound. (M+H)⁺310.

Step B: N-(isothiazol-5-yl)-3-azabicyclo[3.1.0]hexane-6-carboxamide hydrochloride To a solution of tert-butyl 6-(isothiazol-5-ylcarbamoyl)-3-azabicyclo[3.1.0]hexane-3-carboxylate (247 mg, 0.799 mmol, 3 mL MeOH) was added an excess amount of a 4 N HCl in dioxane solution. After addition, the reaction was allowed to stir at ambient temperature for one hour and then concentrated in vacuo to afford title compound which was used without further purification.

Step C: 3-[(2R)-2-hydroxy-2-(4-methyl-1-oxo-1,3-dihydro-2-benzofuran-5-yl)ethyl]-N-(isothiazol-5-yl)-3-azabicyclo[3.1.0]hexane-6-carboxamide hydrochloride N-(isothiazol-5-yl)-3-azabicyclo[3.1.0]hexane-6-carboxamide hydrochloride (110 mg, 0.448 mmol) was diluted in EtOH (4 mL) and treated with triethylamine (312 µL, 2.24 mmol) for 10 minutes. After 10 minutes, 4-methyl-5-[(2R)-oxiran-2-yl]-2-benzofuran-1 (3H)-one (85 mg, 0.448 mmol) was added and the reaction mixture was heated to reflux for 15 hours. Once cooled, the reaction was concentrated in vacuo, purified via prep TLC (ethyl acetate/acetonitrile/methanol/IPA—80/10/8/2) to afford the title compound as a free base. Treatment with excess 1N HCl in Et2O solution afforded the title compound as its hydrochloride salt. (M+H)⁺ 400. Since the starting 3-(tert-butoxycarbonyl)-3-azabicyclo[3.1.0]hexane-6-carboxylic acid has trans stereochemistry the title compound is also the trans isomer.

The following compounds in Table 8 were made in a similar fashion as described for 3-[(2R)-2-hydroxy-2-(4-methyl-1-oxo-1,3-dihydro-2-benzofuran-5-yl)ethyl]-N-(isothiazol-5-yl)-3-azabicyclo[3.1.0]hexane-6-carboxamide hydrochloride (Example 54) starting with 3-(tert-butoxycarbonyl)-3-azabicyclo[3.1.0]hexane-6-carboxylic acid using commercially available or known amines as coupling partners. The products have trans stereochemistry of the cyclopropane in the azabicyclo hexane ring. The initially isolated freebase products were typically converted to the hydrochloride salts as described in Example 54.

TABLE 8

| EXAMPLE | Structure | LC-MS |
|---|---|---|
| 55 | 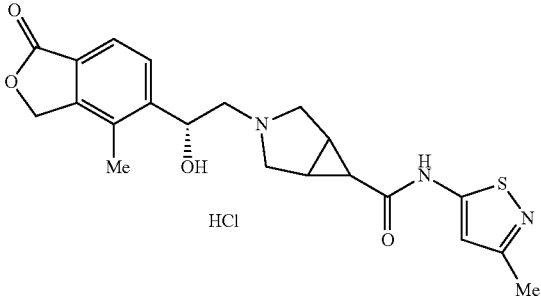 [SMILES: Cc1cc(NC(=O)C2C3CN(C[C@H](O)c4ccc5c(c4C)COC5=O)CC32)sn1 ; Cl] 3-((R)-2-hydroxy-2-(4-methyl-1-oxo-1,3-dihydroisobenzofuran-5-yl)ethyl)-N-(3-methylisothiazol-5-yl)-3-azabicyclo[3.1.0]hexane-6-carboxamide and the hydrochloride salt thereof | 414 (M + H)+ |
| 56 | 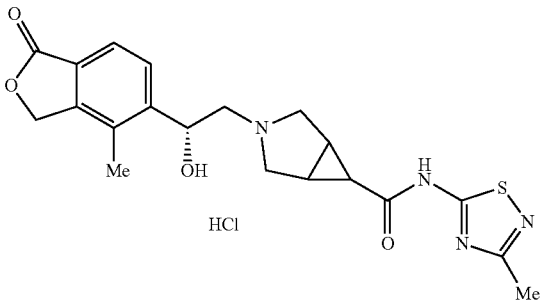 [SMILES: Cc1nsc(NC(=O)C2C3CN(C[C@H](O)c4ccc5c(c4C)COC5=O)CC32)n1 ; Cl] 3-((R)-2-hydroxy-2-(4-methyl-1-oxo-1,3-dihydroisobenzofuran-5-yl)ethyl)-N-(3-methyl-1,2,4-thiadiazol-5-yl)-3-azabicyclo[3.1.0]hexane-6-carboxamide and the hydrochloride salt thereof | 415 (M + H)+ |
| 57 | 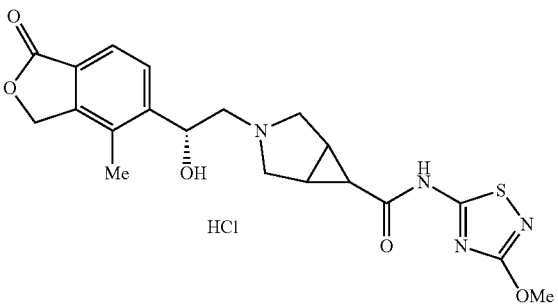 [SMILES: COc1nsc(NC(=O)C2C3CN(C[C@H](O)c4ccc5c(c4C)COC5=O)CC32)n1 ; Cl] 3-((R)-2-hydroxy-2-(4-methyl-1-oxo-1,3-dihydroisobenzofuran-5-yl)ethyl)-N-(3-methoxy-1,2,4-thiadiazol-5-yl)-3-azabicyclo[3.1.0]hexane-6=carboxamide and the hydrochloride salt thereof | 431 (M + H)+ |
| 58 | 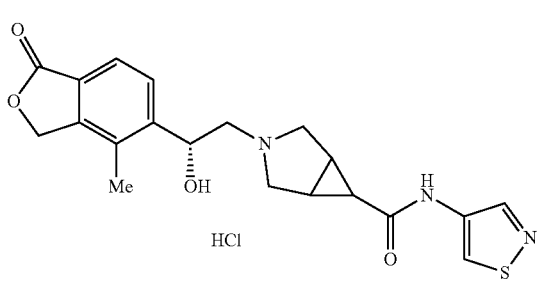 [SMILES: Cc1c([C@@H](O)CN2CC3C(C2)C3C(=O)Nc2cnsc2)ccc2c1COC2=O ; Cl] 3-((R)-2-hydroxy-2-(4-methyl-1-oxo-1,3-dihydroisobenzofuran-5-yl)ethyl)-N-(isothiazol-4-yl)-3-azabicyclo[3.1.0]hexane-6-carboxamide and the hydrochloride salt thereof | 400 (M + H)+ |

TABLE 8-continued

| EXAMPLE | Structure | LC-MS |
|---------|-----------|-------|
| 59 | 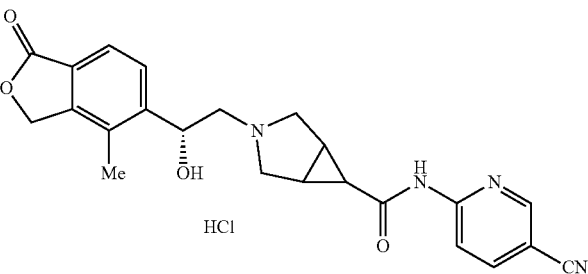 [SMILES: Cc1c([C@@H](O)CN2CC3C(C2)C3C(=O)Nc2ccc(C#N)cn2)ccc2c1COC2=O ; Cl]<br>N-(5-cyanopyridin-2-yl)-3-((R)-2-hydroxy-2-(4-methyl-1-oxo-1,3-dihydroisobenzofuran-5-yl)ethyl)-3-azabicyclo[3.1.0]hexane-6-carboxamide and the hydrochloride salt thereof | 419 (M + H)$^+$ |
| 60 | 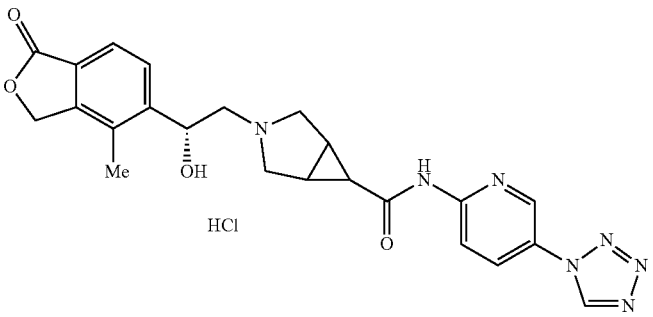 [SMILES: Cc1c([C@@H](O)CN2CC3C(C2)C3C(=O)Nc2ccc(-n3cnnn3)cn2)ccc2c1COC2=O ; Cl]<br>N-(5-(1H-tetrazol-1-yl)pyridin-2-yl)-3-((R)-2-hydroxy-2-(4-methyl-1-oxo-1,3-dihydroisobenzofuran-5-yl)ethyl)-3-azabicyclo[3.1.0]hexane-6-carboxamide and the hydrochloride salt thereof | 462 (M + H)$^+$ |

The following compounds in Table 9 were made in a similar fashion as described for 1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide hydrochloride (Example 41) starting with 3-(tert-butoxycarbonyl)-3-azabicyclo[3.1.0]hexane-6-carboxylic acid using commercially available or known amines as coupling partners, and alkylation of the secondary amides with iodomethane.

TABLE 9

| EXAMPLE | Structure | LC-MS |
|---------|-----------|-------|
| 61 | 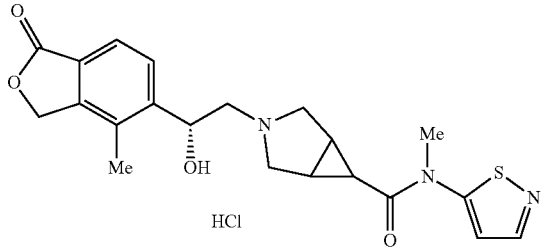 [SMILES: Cc1c([C@@H](O)CN2CC3C(C2)C3C(=O)N(C)c2ccns2)ccc2c1COC2=O ; Cl]<br>3-((R)-2-hydroxy-2-(4-methyl-1-oxo-1,3-dihydroisobenzofuran-5-yl)ethyl)-N-(isothiazol-5-yl)-N-methyl-3-azabicyclo[3.1.0]hexane-6-carboxamide and the hydrochloride salt thereof | 414 (M + H)$^+$ |

TABLE 9-continued

| EXAMPLE | Structure | LC-MS |
|---|---|---|
| 62 | 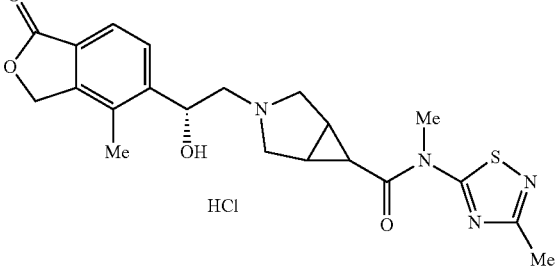 3-((R)-2-hydroxy-2-(4-methyl-1-oxo-1,3-dihydroisobenzofuran-5-yl)ethyl)-N-methyl-N-(3-methyl-1,2,4-thiadiazol-5-yl)-3-azabicyclo[3.1.0]hexane-6-carboxamide and the hydrochloride salt thereof | 429 (M + H)+ |

The following Thallium Flux Assay was performed on each of the final product compounds in the Examples. When the final product of an Example was an HCl salt, the salt was run in the Assay.

THALLIUM FLUX ASSAY

Cell Culture Conditions—HEK293 cells stably expressing hROMK (hKir1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($T_{12}SO_4$) Concentrate (Component G)—50 mM in water. Store at 4° C.
  DMSO (dimethyl sulfoxide, Component H)—1 mL (100%)
Reagent Preparation: FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 µl 1000× FluxOR™ Reagent; 100 µl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use.

Assay protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected from light, for 90 min
5. Remove loading buffer and replace with 25 µl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

Data collected for compounds in the Examples of the present invention using the Thallium Flux Assay are shown in Table 10 below. All of the tested final product compounds in the Examples (diastereomeric mixtures and individual diastereomers) had $IC_{50}$ potencies less than 1 μM in the Thallium Flux Assay.

TABLE 10

| Example No. | Thallium Flux $IC_{50}$ (μM) |
| --- | --- |
| 1 | 0.17 |
| 2 | 0.46 |
| 3 | 0.14 |
| 4 | 0.21 |
| 5 | 0.03 |
| 6 | 0.07 |
| 7 | 0.10 |
| 8 | 0.10 |
| 9 | 0.25 |
| 10 | 0.01 |
| 11 | 0.21 |
| 12 | 0.03 |
| 13 | 0.03 |
| 14 | 0.14 |
| 15 | 0.18 |
| 16 | 0.26 |
| 17 | 0.41 |
| 18 | 0.51 |
| 19 | 0.44 |
| 20 | 0.47 |
| 21 | 0.41 |
| 22 | 0.04 |
| 23 | 0.08 |
| 24 | 0.09 |
| 25 | 0.18 |
| 26 | 0.15 |
| 27 | 0.14 |
| 28 | 0.10 |
| 29 | 0.24 |
| 30 | 0.10 |
| 31 | 0.16 |
| 32 | 0.30 |
| 33 | 0.17 |
| 34 | 0.34 |
| 35 | 0.42 |
| 36 | 0.12 |
| 37 | 0.47 |
| 38 | 0.11 |
| 39 | 0.22 |
| 40 | 0.42 |
| 41 | 0.01 |
| 42 | 0.02 |
| 43 | 0.05 |
| 44 | 0.02 |
| 45 | 0.25 |
| 46 | 0.05 |
| 47 | 0.06 |

TABLE 10-continued

| Example No. | Thallium Flux $IC_{50}$ (μM) |
| --- | --- |
| 48 | 0.04 |
| 49 | 0.20 |
| 50 | 0.37 |
| 51 | 0.22 |
| 52 | 0.26 |
| 53 | 0.26 |
| 54 | 0.16 |
| 55 | 0.06 |
| 56 | 0.35 |
| 57 | 0.31 |
| 58 | 0.28 |
| 59 | 0.40 |
| 60 | 0.47 |
| 61 | 0.14 |
| 62 | 0.17 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

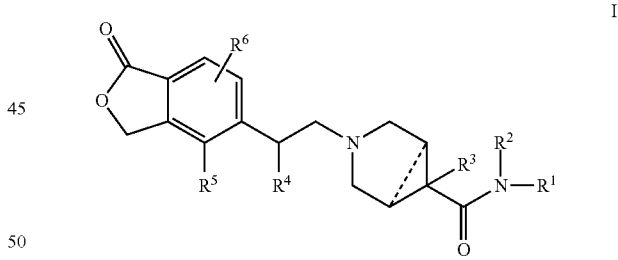

or a pharmaceutically acceptable salt thereof wherein $R^1$ is:

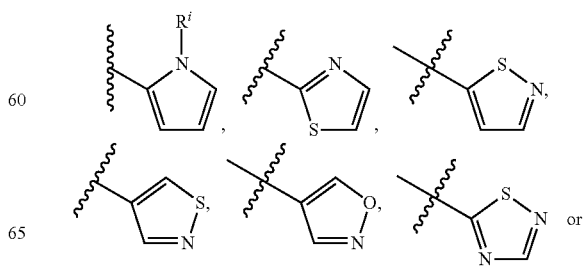

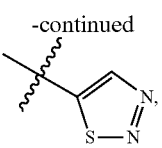

wherein each heterocyclic ring is optionally substituted on an available ring carbon with —$C_{1-3}$alkyl, —$OC_{1-3}$alkyl, —$C_{3-4}$cycloalkyl, —$OC_{3-4}$cycloalkyl or —CN; and $R^i$ is selected from —H or phenyl optionally substituted with $C_{1-3}$alkyl or halo;

$R^2$ is —H or —$C_{1-6}$alkyl;

$R^3$ is —H, —OH, —F or —$NH_2$;

$R^4$ is —H, —OH, oxo, —F or —$C_{1-6}$alkyl;

$R^5$ is —H, halo or —$C_{1-3}$alkyl optionally substituted with one to three of —F;

$R^6$ is —H, halo, —O—$C_{1-3}$alkyl, —C(O)O$C_{1-3}$alkyl or —$C_{1-3}$alkyl optionally substituted with one to three of —F; and the dashed line "- - -" represents the presence or absence of a bond.

2. A compound having structural Formula I

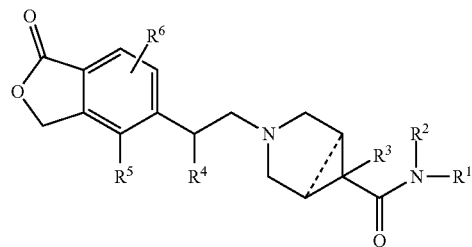

or a pharmaceutically acceptable salt thereof wherein;

$R^1$ is

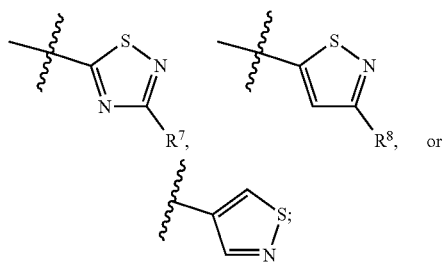

$R^2$ is —H or —$C_{1-3}$alkyl;
$R^3$ is —H, —F or —$NH_2$;
$R^4$ is —H or —OH;
$R^5$ is —H, halo, —$CH_3$ or —$CF_3$;
$R^6$ is —H;
$R^7$ is —H, —$C_{1-3}$alkyl or —$OC_{1-3}$alkyl;
$R^8$ is —H, —$C_{1-3}$alkyl or —$OC_{1-3}$alkyl; and
the dashed line "- - -" represents the presence or absence of a bond.

3. The compound of claim 1 selected from:

N-(4-cyano-1-(4-fluorophenyl)-1H-pyrrol-2-yl)-1-(2-(1-oxo-1,3-dihydroisobenzofuran-5-yl)ethyl)piperidine-4-carboxamide;

1-[(2R)-2-hydroxy-2-(4-methyl-1-oxo-1,3-dihydro-2-benzofuran-5-yl)ethyl]-N-(isothiazol-5-yl)piperidine-4-carboxamide;

(R)-1-(2-hydroxy-2-(4-methyl-1-oxo-1,3-dihydroisobenzofuran-5-yl)ethyl)-N-(isoxazol-4-yl)piperidine-4-carboxamide;

(R)-1-(2-hydroxy-2-(4-methyl-1-oxo-1,3-dihydroisobenzofuran-5-yl)ethyl)-N-(isothiazol-4-yl)piperidine-4-carboxamide;

(R)-N-(4-cyanothiazol-2-yl)-1-(2-hydroxy-2-(4-methyl-1-oxo-1,3-dihydroisobenzofuran-5-yl)ethyl)piperidine-4-carboxamide;

(R)-1-(2-hydroxy-2-(4-methyl-1-oxo-1,3-dihydroisobenzofuran-5-yl)ethyl)-N-(isothiazolo[4,3-c]pyridin-3-yl)piperidine-4-carboxamide;

(R)-1-(2-hydroxy-2-(4-methyl-1-oxo-1,3-dihydroisobenzofuran-5-yl)ethyl)-N-(isothiazolo[4,3-c]pyridin-3-yl)piperidine-4-carboxamide;

(R)-1-(2-hydroxy-2-(4-methyl-1-oxo-1,3-dihydroisobenzofuran-5-yl)ethyl)-N-(3-methyl-1,2,4-thiadiazol-5-yl)piperidine-4-carboxamide;

(R)-N-(3-cyclopropyl-1,2,4-thiadiazol-5-yl)-1-(2-hydroxy-2-(4-methyl-1-oxo-1,3-dihydroisobenzofuran-5-yl)ethyl)piperidine-4-carboxamide;

(R)-1-(2-hydroxy-2-(4-methyl-1-oxo-1,3-dihydroisobenzofuran-5-yl)ethyl)-N-(3-methylisothiazol-5-yl)piperidine-4-carboxamide;

(R)-4-hydroxy-1-(2-hydroxy-2-(4-methyl-1-oxo-1,3-dihydroisobenzofuran-5-yl)ethyl)-N-(isothiazol-5-yl)piperidine-4-carboxamide;

(R)-4-hydroxy-1-(2-hydroxy-2-(4-methyl-1-oxo-1,3-dihydroisobenzofuran-5-yl)ethyl)-N-(3-methylisothiazol-5-yl)piperidine-4-carboxamide;

(R)-4-hydroxy-1-(2-hydroxy-2-(4-methyl-1-oxo-1,3-dihydroisobenzofuran-5-yl)ethyl)-N-(3-methyl-1,2,4-thiadiazol-5-yl)piperidine-4-carboxamide;

1-[(2R)-2-hydroxy-2-(4-methyl-1-oxo-1,3-dihydro-2-benzofuran-5-yl)ethyl]-N-(isothiazol-5-yl)-N-methylpiperidine-4-carboxamide;

1-[(2R)-2-hydroxy-2-(4-methyl-1-oxo-1,3-dihydro-2-benzofuran-5-yl)ethyl]-N-(isothiazol-5-yl)-N-trideuteromethylpiperidine-4-carboxamide;

(R)-N-ethyl-1-(2-hydroxy-2-(4-methyl-1-oxo-1,3-dihydroisobenzofuran-5-yl)ethyl)-N-(isothiazol-5-yl)piperidine-4-carboxamide;

(R)-1-(2-hydroxy-2-(4-methyl-1-oxo-1,3-dihydroisobenzofuran-5-yl)ethyl)-N-methyl-N-(3-methylisothiazol-5-yl)piperidine-4-carboxamide;

(R)-1-(2-hydroxy-2-(4-methyl-1-oxo-1,3-dihydroisobenzofuran-5-yl)ethyl)-N-(3-methoxy-1,2,4-thiadiazol-5-yl)-N-methylpiperidine-4-carboxamide;

4-amino-1-[(2R)-2-hydroxy-2-(4-methyl-1-oxo-1,3-dihydro-2-benzofuran-5-yl)ethyl]-N-(isothiazol-5-yl)piperidine-4-carboxamide;

4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide;

(R)-4-fluoro-1-(2-hydroxy-2-(4-methyl-1-oxo-1,3-dihydroisobenzofuran-5-yl)ethyl)-N-(3-methylisothiazol-5-yl)piperidine-4-carboxamide;

(R)-5-(2-(4-(2,3-dihydro-1H-pyrrolo[3,2-c]pyridine-1-carbonyl)-4-fluoropiperidin-1-yl)-1-hydroxyethyl)-4-methylisobenzofuran-1 (3H)-one;

(R)-4-fluoro-1-(2-hydroxy-2-(4-methyl-1-oxo-1,3-dihydroisobenzofuran-5-yl)ethyl)-N-(isothiazol-4-yl)piperidine-4-carboxamide;

(R)-4-fluoro-1-(2-hydroxy-2-(4-methyl-1-oxo-1,3-dihydroisobenzofuran-5-yl)ethyl)-N-(1,2,3-thiadiazol-5-yl)piperidine-4-carboxamide;

3-[(2R)-2-hydroxy-2-(4-methyl-1-oxo-1,3-dihydro-2-benzofuran-5-yl)ethyl]-N-(isothiazol-5-yl)-3-azabicyclo[3.1.0]hexane-6-carboxamide;

3-((R)-2-hydroxy-2-(4-methyl-1-oxo-1,3-dihydroisobenzofuran-5-yl)ethyl)-N-(3-methylisothiazol-5-yl)-3-azabicyclo[3.1.0]hexane-6-carboxamide;

3-((R)-2-hydroxy-2-(4-methyl-1-oxo-1,3-dihydroisobenzofuran-5-yl)ethyl)-N-(3-methyl-1,2,4-thiadiazol-5-yl)-3-azabicyclo[3.1.0]hexane-6-carboxamide;

3-((R)-2-hydroxy-2-(4-methyl-1-oxo-1,3-dihydroisobenzofuran-5-yl)ethyl)-N-(3-methoxy-1,2,4-thiadiazol-5-yl)-3-azabicyclo[3.1.0]hexane-6-carboxamide;

3-((R)-2-hydroxy-2-(4-methyl-1-oxo-1,3-dihydroisobenzofuran-5-yl)ethyl)-N-(isothiazol-4-yl)-3-azabicyclo[3.1.0]hexane-6-carboxamide;

3-((R)-2-hydroxy-2-(4-methyl-1-oxo-1,3-dihydroisobenzofuran-5-yl)ethyl)-N-(isothiazol-5-yl)-N-methyl-3-azabicyclo[3.1.0]hexane-6-carboxamide; or 3-((R)-2-hydroxy-2-(4-methyl-1-oxo-1,3-dihydroisobenzofuran-5-yl)ethyl)-N-methyl-N-(3-methyl-1,2,4-thiadiazol-5-yl)-3-azabicyclo[3.1.0]hexane-6-carboxamide;

or a pharmaceutically acceptable salt thereof.

4. A compound selected from:

(R)-1-(2-Hydroxy-2-(4-methyl-1-oxo-1,3-dihydroisobenzofuran-5-yl)ethyl)-N-(3-methoxy-1,2,4-thiadiazol-5-yl)piperidine-4-carboxamide;

1-[(2R)-2-hydroxy-2-(4-methyl-1-oxo-1,3-dihydro-2-benzofuran-5-yl)ethyl]-N-(isothiazol-5-yl)piperidine-4-carboxamide;

(R)-1-(2-hydroxy-2-(4-methyl-1-oxo-1,3-dihydroisobenzofuran-5-yl)ethyl)-N-(isothiazol-4-yl)piperidine-4-carboxamide;

(R)-1-(2-hydroxy-2-(4-methyl-1-oxo-1,3-dihydroisobenzofuran-5-yl)ethyl)-N-(3-methyl-1,2,4-thiadiazol-5-yl)piperidine-4-carboxamide;

1-[(2R)-2-hydroxy-2-(4-methyl-1-oxo-1,3-dihydro-2-benzofuran-5-yl)ethyl]-N-(isothiazol-5-yl)-N-methyl-piperidine-4-carboxamide;

1-[(2R)-2-hydroxy-2-(4-methyl-1-oxo-1,3-dihydro-2-benzofuran-5-yl)ethyl]-N-(isothiazol-5-yl)-N-trideuteromethylpiperidine-4-carboxamide;

(R)-N-ethyl-1-(2-hydroxy-2-(4-methyl-1-oxo-1,3-dihydroisobenzofuran-5-yl)ethyl)-N-(isothiazol-5-yl)piperidine-4-carboxamide;

(R)-1-(2-hydroxy-2-(4-methyl-1-oxo-1,3-dihydroisobenzofuran-5-yl)ethyl)-N-methyl-N-(3-methylisothiazol-5-yl)piperidine-4-carboxamide;

(R)-1-(2-hydroxy-2-(4-methyl-1-oxo-1,3-dihydroisobenzofuran-5-yl)ethyl)-N-(3-methoxy-1,2,4-thiadiazol-5-yl)-N-methylpiperidine-4-carboxamide;

4-amino-1-[(2R)-2-hydroxy-2-(4-methyl-1-oxo-1,3-dihydro-2-benzofuran-5-yl)ethyl]-N-(isothiazol-5-yl)piperidine-4-carboxamide 4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide; or 3-((R)-2-hydroxy-2-(4-methyl-1-oxo-1,3-dihydroisobenzofuran-5-yl)ethyl)-N-(isothiazol-5-yl)-N-methyl-3-azabicyclo[3.1.0]hexane-6-carboxamide; or a pharmaceutically acceptable salt thereof.

5. A compound selected from:

(R)-1-(2-Hydroxy-2-(4-methyl-1-oxo-1,3-dihydroisobenzofuran-5-yl)ethyl)-N-(3-methoxy-1,2,4-thiadiazol-5-yl)piperidine-4-carboxamide;

1-[(2R)-2-hydroxy-2-(4-methyl-1-oxo-1,3-dihydro-2-benzofuran-5-yl)ethyl]-N-(isothiazol-5-yl)piperidine-4-carboxamide;

1-[(2R)-2-hydroxy-2-(4-methyl-1-oxo-1,3-dihydro-2-benzofuran-5-yl)ethyl]-N-(isothiazol-5-yl)-N-methyl-piperidine-4-carboxamide;

(R)-N-ethyl-1-(2-hydroxy-2-(4-methyl-1-oxo-1,3-dihydroisobenzofuran-5-yl)ethyl)-N-(isothiazol-5-yl)piperidine-4-carboxamide; or 4-fluoro-1-[(2R)-2-hydroxy-2-(4-methyl-1-oxo-1,3-dihydro-2-benzofuran-5-yl)ethyl]-N-(isothiazol-5-yl)piperidine-4-carboxamide;

or a pharmaceutically acceptable salt thereof.

6. A pharmaceutical composition comprised of a compound of claim 1 or a pharmaceutically acceptable salt thereof and a pharmaceutically acceptable carrier.

7. The pharmaceutical composition of claim 6 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pro-drug thereof, or a pharmaceutically acceptable salt of any of the foregoing.

8. A method for causing diueresis, natriuresis or both, in a patient in need thereof by administering a compound of claim 1.

9. A method for treating hypertension in a patient in need thereof by administering a compound of claim 1.

* * * * *